United States Patent
Rezayat

(10) Patent No.: US 10,371,684 B1
(45) Date of Patent: *Aug. 6, 2019

(54) SEALED CONTAINER SENSOR DEVICE

(71) Applicant: Mohsen Rezayat, Cincinnati, OH (US)

(72) Inventor: Mohsen Rezayat, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/278,401

(22) Filed: Feb. 18, 2019

Related U.S. Application Data

(63) Continuation of application No. 15/093,109, filed on Apr. 7, 2016, now Pat. No. 10,254,265.

(60) Provisional application No. 62/145,672, filed on Apr. 10, 2015.

(51) Int. Cl.
*G01N 33/14* (2006.01)
*H04W 88/02* (2009.01)

(52) U.S. Cl.
CPC ......... *G01N 33/146* (2013.01); *G01N 33/143* (2013.01); *H04W 88/02* (2013.01)

(58) Field of Classification Search
CPC .................... G01N 33/146; G01N 33/143
See application file for complete search history.

(56) References Cited

U.S. PATENT DOCUMENTS

| | | | |
|---|---|---|---|
| 2001/0040911 A1* | 11/2001 | Rubenstein | G01K 1/14 374/141 |
| 2005/0190070 A1* | 9/2005 | Rudduck | B65D 39/12 340/693.5 |
| 2007/0108048 A1* | 5/2007 | Wang | C12Q 1/001 204/403.01 |
| 2007/0151869 A1* | 7/2007 | Heller | C12Q 1/006 205/792 |
| 2010/0202492 A1* | 8/2010 | Larimer | G01K 13/00 374/185 |
| 2013/0206760 A1* | 8/2013 | Susko | G01D 11/245 220/88.3 |
| 2015/0330940 A1* | 11/2015 | Schneider | G01N 27/414 257/253 |
| 2015/0355012 A1* | 12/2015 | Gurumohan | A47G 19/00 702/55 |

* cited by examiner

*Primary Examiner* — Christine A Enad
(74) *Attorney, Agent, or Firm* — Frost Brown Todd LLC

(57) ABSTRACT

A system for managing and monitoring a small or large collection of sealed containers, such as wine bottles, barrels, medicine containers, or bags, as well as individual grapes, batches of must, and other liquids, whose contents may be volatile and difficult to access without destroying the seal and the contents or risking contamination of the liquid. The system performs automated monitoring tasks by communicating with specially manufactured bottles or traditional bottles that have had a sensor installed. Sensor installation can be accomplished with unmodified commercialy available equipment.

20 Claims, 26 Drawing Sheets

SEALED CONTAINER SENSOR DEVICE

PRIORITY

This application is a continuation of U.S. Non-Provisional patent application Ser. No. 15/093,109 filed Apr. 7, 2016, which itself claims priority to U.S. Provisional Patent Application Ser. No. 62/145,672 filed Apr. 10, 2015, each entitled "Sealed Container Sensor Device," the disclosure of each of which are incorporated by reference herein.

FIELD

The disclosed technology pertains to a system for installing one or more electro-chemical micro-sensors, optical micro-sensors, humidity micro-sensors, temperature micro-sensors, or other sensors and micro-sensors (from here on simply referred to as sensor) on a sealed container to allow interaction with the contents while statically maintaining the sealed environment.

BACKGROUND

Liquid medicines, vaccines, perfumes, wines and other fluids that are contained in a sealed container are currently very difficult to monitor and control. In addition to natural aging, elements such as heat, humidity, light, oxygen and even excessive vibration could dramatically affect the chemical composition of what is contained within the sealed container. For instance, when wine is bottled, it is necessary to control the liquid and gas contents of the bottle as it is sealed to ensure proper aging and prevent spoilage. Some wines may turn into vinegar if there is even a small amount of oxygen, bacteria, or other contamination present, while others may actually improve over time with the right mixture of gases present. Regardless of the mix of liquids and gasses present, stability of the contents and an uncompromised seal is critical.

For collectors of wine, controlling and monitoring the contents of valuable bottles is a major challenge. Even with complex wine vaults that carefully control temperature, humidity, light, and movement, a bottle of wine may still be ruined despite not being visibly opened or contaminated. Fraud can also be a problem, with expensive bottles of wine being refilled with cheaper contents and resold as new. However, checking the contents of a wine bottle for their quality or authenticity is most commonly accomplished by destroying the seal and opening the bottle, with the result that the only way to verify and monitor a valuable investment is by destroying it in the process.

Even if a handheld device were readily available to allow wine to be tested without destroying the seal and initiating the spoiling process, such a device would be of limited use in monitoring a significant collection of bottles or even a small collection of extremely valuable bottles. For example, such a device would require the bottle to be regularly removed from storage and handled, which could cause harmful stirring of the contents, changes in temperature, exposure to light or contaminants, risk of accidental breakage, and other detrimental effects.

What is needed, therefore, is an improved system for monitoring the contents of a sealed container while statically maintaining the sealed environment.

BRIEF DESCRIPTION OF THE DRAWINGS

The drawings and detailed description that follow are intended to be merely illustrative and are not intended to limit the scope of the invention as contemplated by the inventor.

DETAILED DESCRIPTION

The inventor has conceived of novel technology that, for the purpose of illustration, is disclosed herein as applied in the context of a sensor device and software application used to monitor and manage one or more sealed containers such as wine bottles. While the disclosed applications of the inventor's technology satisfy a long-felt but unmet need in the art of the management and remote monitoring of sealed containers such as wine bottles, it should be understood that the inventor's technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

The invention is applicable beyond wine to other fluids, such as liquid medicine, vaccines, and perfumes that are contained within a sealed bottle. For instance, extreme temperatures, humidity, and light could have a negative impact on medicines and vaccines causing them to physically change, lose potency, or even threaten a patient's health. Currently, the only indicators that something could be wrong are the expiration date and a change in odor or color. With embedded sensors, we could do a much better job of understanding what the medicine/vaccine is doing inside the sealed container and use it so long as the chemical parameters are within an acceptable range. Therefore, everything stated below about wine should be considered as equally applicable (for the most parts) to these other sealed fluids beyond wine. Additionally, while discussion often refers to the sensor being used on a sealed container as one exemplary use, it will be apparent in light of the disclosure herein that the sensor may equally be used on liquids in unsealed containers.

I. Exemplary System for Monitoring and Management of Sealed Containers

Figure 1:
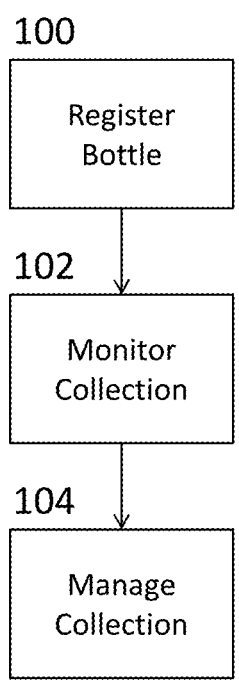
FIG. 1 is a flowchart of a set of high level exemplary steps that a system could perform to allow the monitoring and management of sealed containers.
Figure 7:
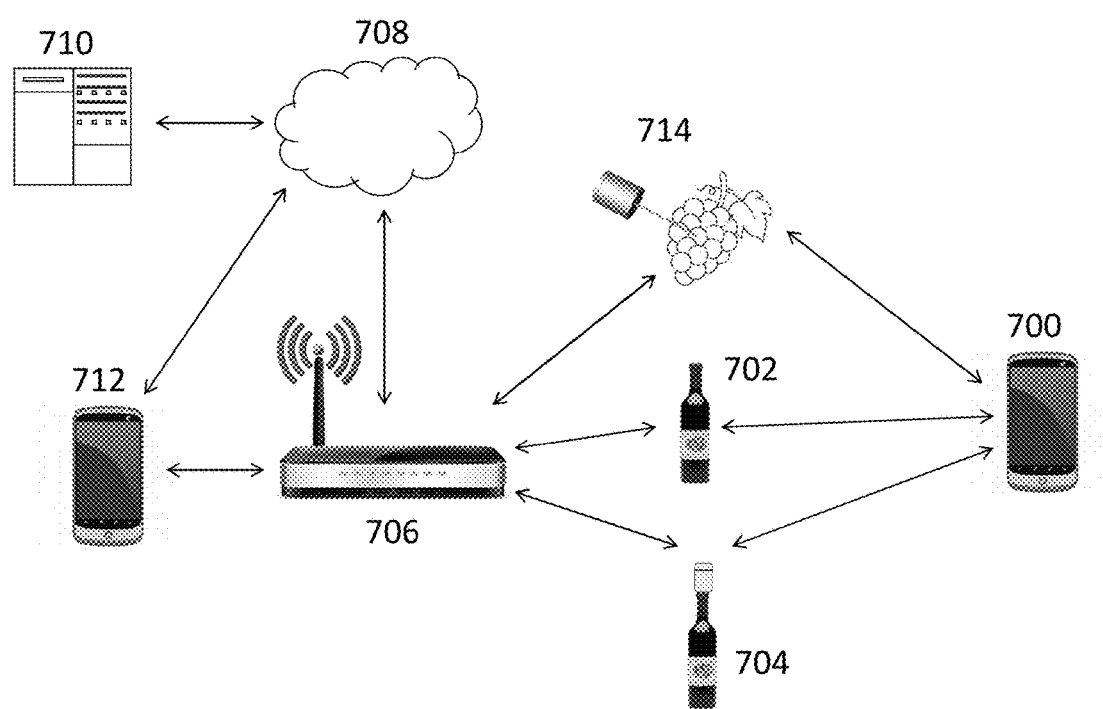
FIG. 7 is a schematic diagram of an exemplary system configured to allow the monitoring and management of one or more sealed container sensor devices.

Turning now to the figures, FIG. 1 shows a flowchart of a set of high level exemplary steps that a system, such as the exemplary system shown in FIG. 7, could perform to allow the monitoring and management of sealed containers. The system of FIG. 7 allows one or more user devices (700, 712) to communicate with a sensor enabled container (702, 704) to collect data from the sensors within the containers. Containers that may work with a sensor could be bottles, cans, barrels, vacuum packages, liquid holding sacks or bags, or any other man-made or naturally occuring container that may store liquids or gases that may desirably be monitored. In some embodiments, the user device (700) may communicate directly with a sensor enabled container (702, 704) via Bluetooth, NFC, infrared, Wi-Fi, or other wireless communication. In some embodiments, the user device (712) may communicate with a sensor enabled container (702, 704), which may also be referred to as a "smart container" or "smart bottle," via a router (706) or other wireless access point or hub via Wi-Fi, Bluetooth, or other wireless communication. In some embodiments, a sensor enabled container may be an integrated sensor bottle (702), wherein the sensor device is integrated with the container at the time of sealing. In some embodiments, the sensor device is contained within a modular device that is installed on a traditional bottle to create an installed sensor bottle (704). A user device (712) or router (706) may also communicate with a server (710) via the internet (708) to both provide information from sensor enabled containers (702, 704) and user devices (700, 712) to the server (710) and also to receive information from the server (710) for use by the user devices (700, 712) and sensor enabled containers (702, 704).

The system of FIG. 7 may also function with a sensor being used as a standalone sensor (714) that may from time to time be used to measure the current composition of a variety of liquids and objects. For example, the standalone sensor (714) may, in addition to being installed on a bottle or other container, be used to measure the composition of a single grape from a vineyards vine, to measure the composition of a "must", which is a batch of pressed grapes including juice, skins, and seeds that is created at early stage of wine making, be used to measure near-finished just as it is bottled, or used to measure wine after a bottle is opened. In this manner, a single sensor can be used to repeatedly measure properties of grapes as they moves from a vine, to a batch of must, to a barrel, to a bottle, and then to a table. This allows for consistency in measuring and minimizes measurement device specific variances.

At a high level, the system of FIG. 7 and similar embodiments allow a user to register containers or bottles (100), automatically monitor one or more containers or bottles (102), and manage one or more containers or bottles (104). Registering bottles (100) configures the system so that it can uniquely identify and communicate with a particular bottle. When monitoring (102) a collection, the system may automatically or semi-automatically communicates with one or more registered bottles and reports the sensed parameters to a user device (700, 712) or the server (710) as well as analysis, messages, or alerts based upon the reported parameters. When managing (104) a collection, the system may provide a variety of user functionality such as comparing parameters of a bottle to parameters of other bottles stored on the server (710), estimating values of registered bottles, exchanging bottles with other users of the system, and reviewing measured parameters of registered bottles. While FIG. 7 shows user devices as being mobile devices, it should be understood that a user device could also be a laptop or desktop computer or another computing device that is capable of sending and receiving information across a wireless network, processing information, displaying information, and receiving user interactions.

II. Exemplary Sealed Container Sensor Device and Methods of Use

Figure 2:
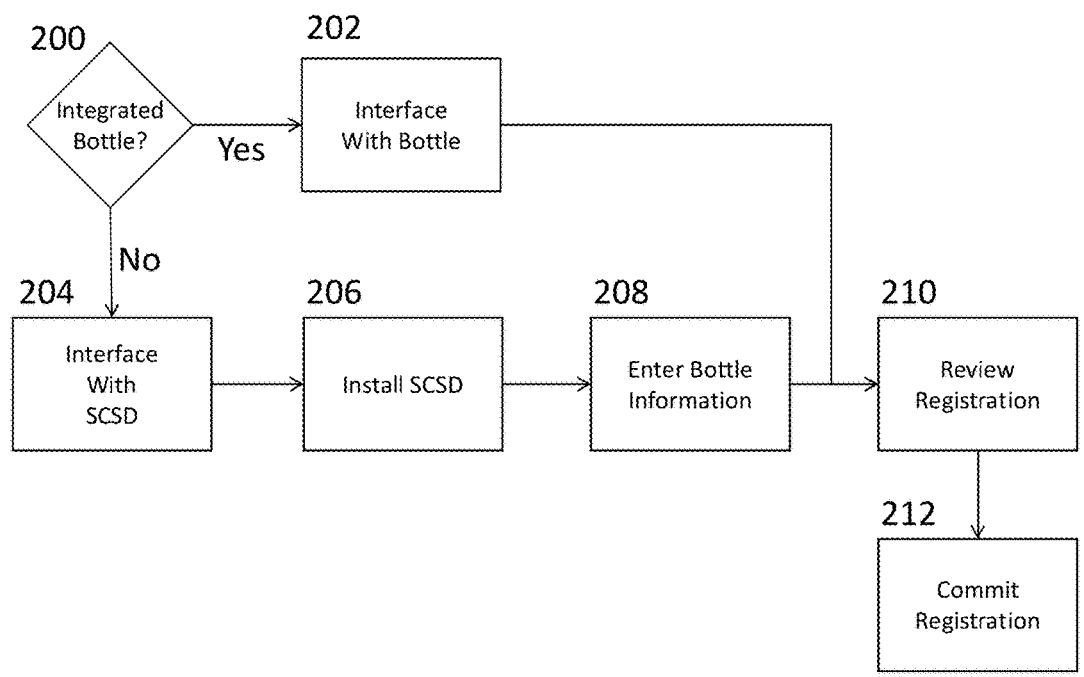
FIG. 2 is a flowchart of a set of exemplary steps that a system could perform to register and configure an additional sealed container.

Turning now to FIG. 2, that figure shows a flowchart of a set of exemplary steps that a system could perform to register and configure an additional sealed container. Initially it must be determined if the bottle to register is an integrated sensor bottle (702) or a traditional bottle. If the bottle is an integrated bottle (200), shown in FIGS. 14-16, the sensor of the integrated bottle must be interfaced (202) with in order to establish communication with the bottle and gather initial information. Interfacing can be accomplished by, for example, using a user device (700, 712) to scan a barcode, QR code, or other unique visual identifier, using a user device (700, 712) to contact the sensor via RFID, Bluetooth, Wi-Fi, NFC, or other wireless communication, or connecting the integrated sensor to the user device (700, 712) via USB, micro-USB, RJ45, or other hardwired connection. Interfacing a user device (700, 712) with a sensor provides a user device with a unique identifier for the interfaced sensor, may cause the sensor and user device to be configured for future communication, and may also provide additional information to the user device related to the interfaced integrated sensor.

For example, using an imaging capability of a user device (700, 712) to scan a barcode on an integrated sensor may cause the user device to receive information via its imaging capability of a unique identification number for the scanned integrated sensor. The user device (700, 712), or server (710), or both may then store the unique identification number so that future interactions with the integrated sensor can be uniquely associated with that integrated sensor and bottle. As another example, the integrated sensor may have a wireless communication capability that waits for a connection from a user device. When a user device connects to the integrated sensor, the integrated sensor may configure itself for automatic future connections to the user device (700, 712) or a router (706) shared with the user device. As another example, an integrated sensor may be configured upon creation to automatically connect to a wireless network with a pre-defined SSID or name, using pre-defined access credentials, so that when a properly configured network is within range the integrated sensor automatically connects and broadcasts its ability to communicate with a user device (700, 712). As another example, the integrated sensor may initially be connected to a user device (700, 712) via USB or other hardwired connection, and the user device may then be used to further configure the integrated sensor for communication over a particular network or with a particular device. Other methods of initially interfacing the integrated sensor with a device or network will be apparent in light of this disclosure.

In addition to providing a unique identifier and configuring the integrated sensor and user device for future communication, interfacing may provide additional information about the contents of the bottle associated with the integrated sensor. For example, scanning a QR code or initially interfacing with an integrated sensor via Bluetooth or Wi-Fi may cause the user device (700, 712) to receive information identifying the origin, age, producer, bottle size, flavor, or other characteristics known at the time the bottle is sealed. In this manner, the information may be automatically received by the user device (700, 712) to ensure accuracy and avoid time consuming manual entry.

Figure 8:
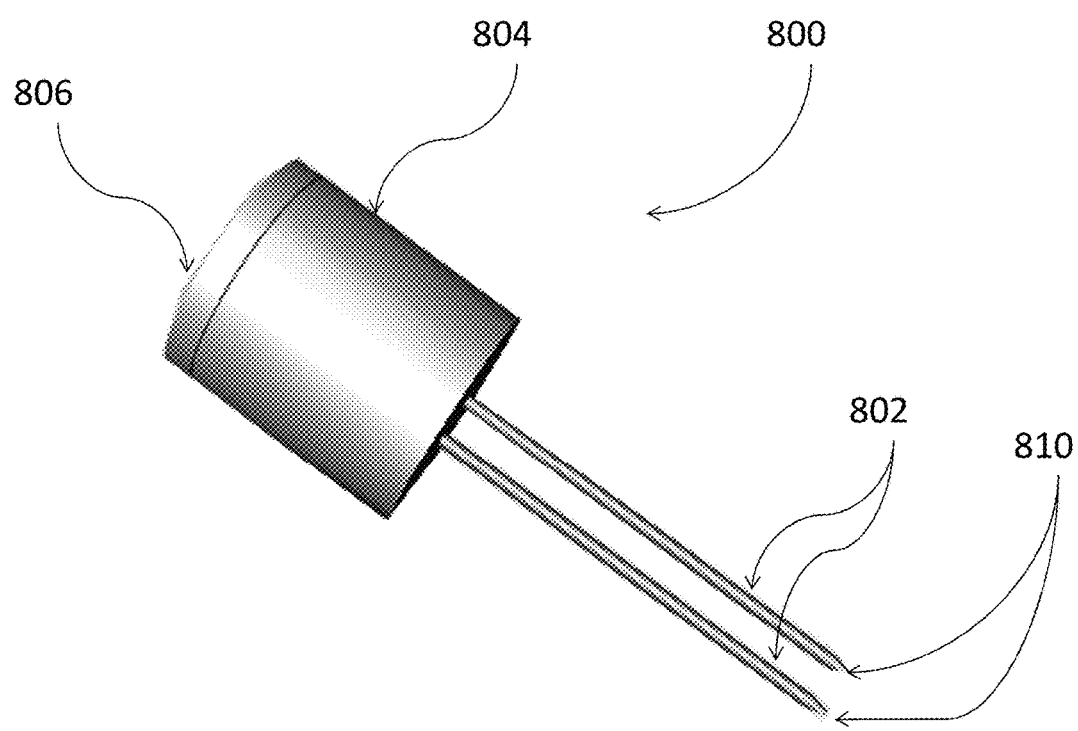
FIG. 8 is a side elevation view of an exemplary sensor device.
Figure 12:
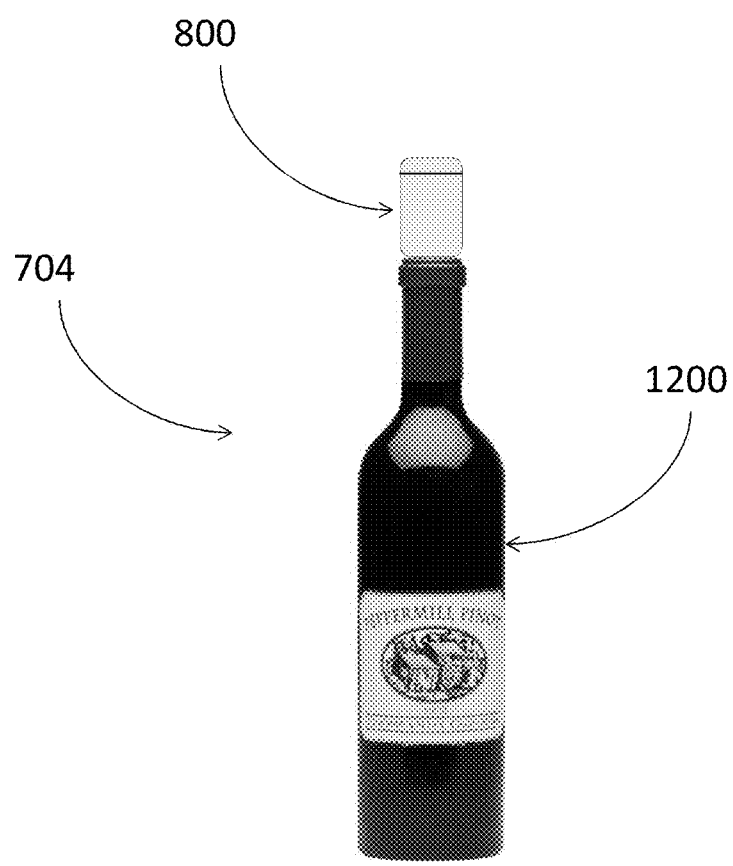
FIG. 12 is a side elevation view of an exemplary sealed container with installed sensor device.

If the bottle being registered does not have an integrated sensor (200), an external sensor may be used instead, such as the sealed container sensor device ("SCSD") (800) shown in FIG. 8 and shown on an installed sensor bottle (704) in FIG. 12. When used, the SCSD (800) may be interfaced with (204) before being installed on a bottle. Interfacing (204) with the SCSD (800) is similar to interfacing with an integrated sensor bottle (202), and may be achieved by barcode, QR code, wireless communication, hardwired communication, or other known methods of initiating communication between the SCSD (800) and a user device (700, 712). Interfacing with an SCSD (800) may not provide the same set of information as an integrated sensor device (702) since an SCSD (800) is installed after a bottle is sealed, and so cannot be configured to provide information on a bottle's contents to a user device (700, 712). However, interfacing with an SCSD (800) may still provide a unique identifier and automated configuration of communication with a user device (700, 712). When a bottle with an installed SCSD (800) is sold or consumed, or otherwise no longer requires monitoring, the SCSD (800) may be removed and installed on a different bottle by, for example, returning the device to its original configuration and repeating the interfacing (204) steps, or by manual editing of the registration via the user device (700, 712).

Figure 6:
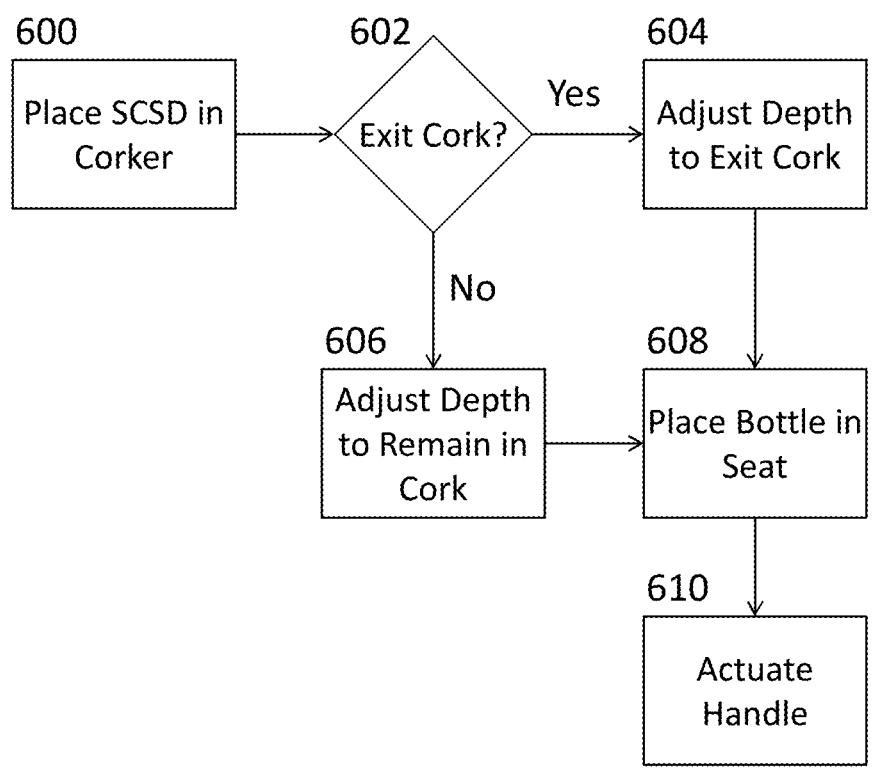
FIG. 6 is a flowchart of set of exemplary steps that could be performed to install a sensor within a sealed container.
Figure 13:
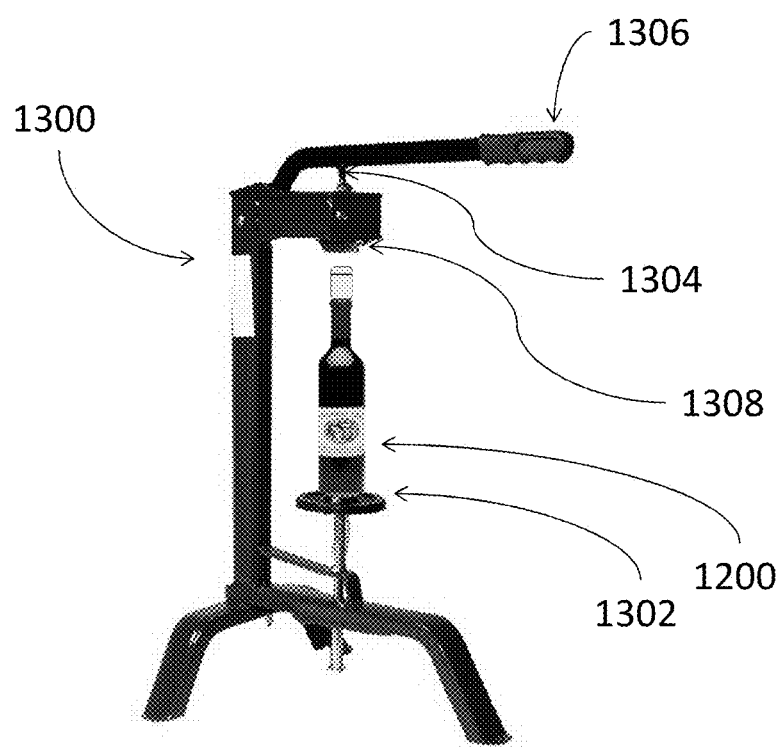
FIG. 13 is a side elevation view of an exemplary tool used for installing or removing a sensor device.

The SCSD (800) may also be installed (206) on a traditional bottle to create an installed sensor bottle (704). Installation of the SCSD (800) may be achieved by using an unmodified bottle corking device to guide and lower the SCSD (800) as it pierces and is seated within the original cork seal of a bottle, as shown in FIGS. 6, 12 and 13 and described in more detail below. Installation of the SCSD (800) will be covered in more detail below. Information for the bottle may be entered (208) by a user and associated with an interfaced SCSD (800). This manual entry of information may include one or more characteristics of the contents of the installed sensor bottle (704), such as origin, date of bottling, flavor, producer, and other information. Entered information is received by the user device (700, 712) and associated with an SCSD (800) unique identifier, so that an installed sensor bottle (704) can be uniquely identified along with its associated entered (208) characteristics. In the event that an SCSD (800) is reused, information may be entered (208) for the new bottle on which the SCSD (800) has been installed, with such information replacing the prior registration and creating a new set of container history and records on the user device (700, 712), server (710), or both.

Once a sensor has been interfaced with (202, 204) and information on the bottle has been received, either automatically during interfacing or via manual entry (208), information for the bottle being registered may be reviewed (210) and committed (212) to the system. When reviewing information, the user device (700, 712) may display the unique identifier for the new integrated or installed sensor bottle, may display information about the established communication type and signal strength (e.g. if communication is via Wi-Fi connection through a router (706) and local area network, signal strength, SSID, or other characteristics of a wireless network may be displayed), and may display information on the bottle that is being added, such as origin, flavor, or producer. After reviewing such displayed information, a user may, via the user device (700, 712) commit (212) the registration causing it to be saved to the user device (700, 712), server (706), or both.

Figure 3:
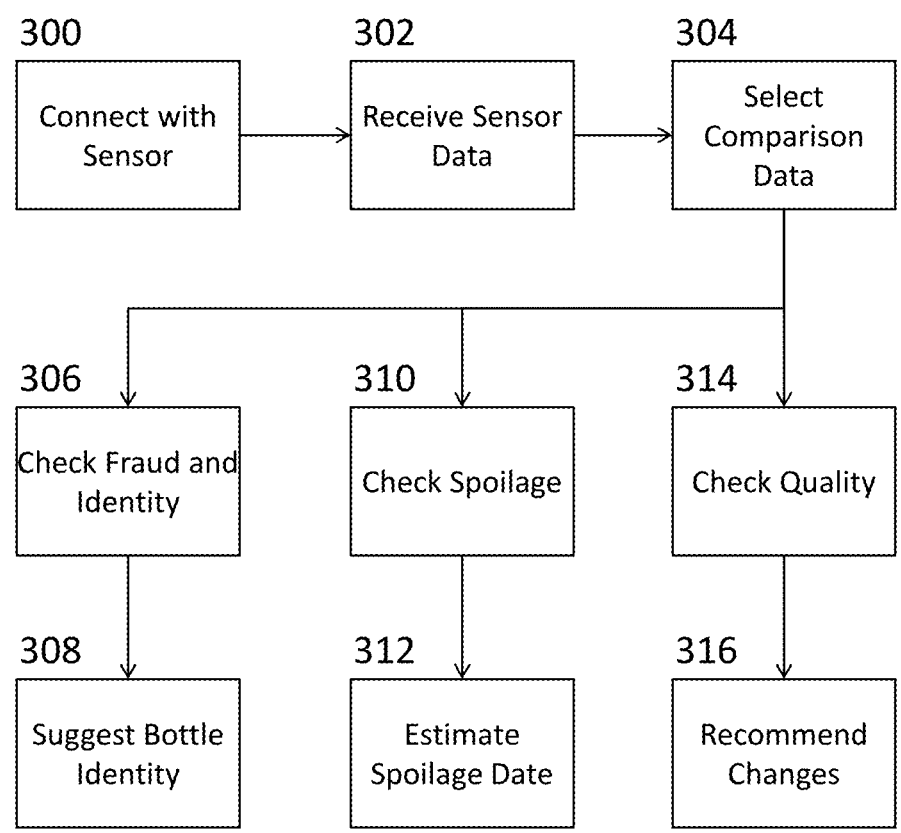
FIG. 3 is a flowchart of a set of exemplary steps that a system could perform to monitor the contents of a sealed container.
Figure 5:
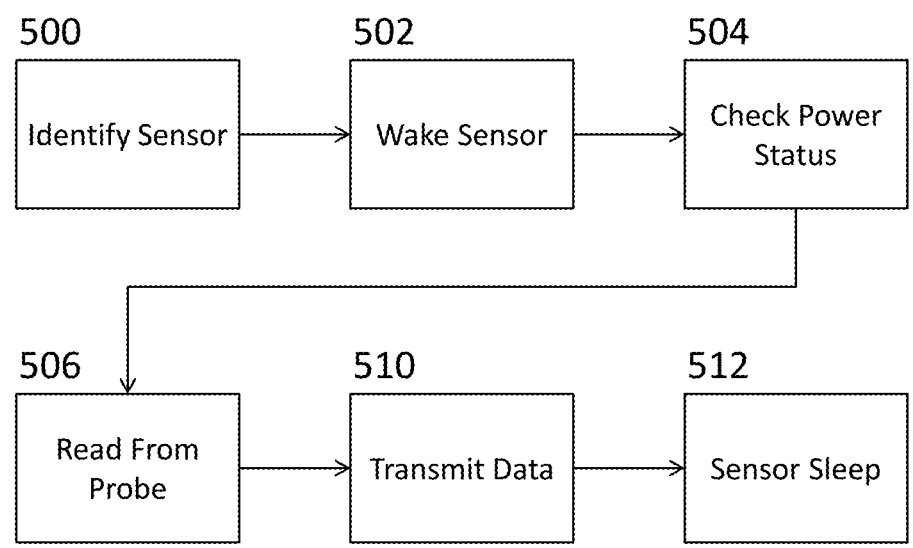
FIG. 5 is a flowchart of a set of exemplary steps that a system could perform to receive data from a sensor while conserving power.

Turning now to FIG. 3, that figures shows a flowchart of a set of exemplary steps that a system could perform to monitor the contents of one or more registered bottles or sealed containers. In order to monitor a sensor enabled bottle, the user device (700, 712) may connect (300) to the sensor of the sensor enabled bottle, whether SCSD or an integrated sensor, via the connection established during registration. This connection may occur periodically, and may be triggered by either the user device (700, 712) or the sensor, depending upon a particular embodiment. As shown in FIG. 5 and described below, some embodiments of the sensor may be in a sleep state when not in active use. Once connected (300) to a sensor, the user device (700, 712) receives data from the sensor, the received data comprising a set of measurements for one or more parameters that the sensor device is configured to measure. Parameters measured may vary by embodiment; in the context of a sensor configured to monitor a bottle of wine, the parameters could include dissolved oxygen, acetic acid, alcohol content, sugar level, pH level, temperature, tannin levels, sulfur dioxide levels, phenol content, and the presence of clarified agents such as egg-whites, gelatin, isinglass, liquid tannin, charcoal, or clays, as well as other known measurable characteristics that may indicate spoilage, ideal flavor, improper storage conditions, or other information.

Once a set of sensor data has been received (302), a comparison data maybe selected from data available on the user device (700, 712), or server (710), or both. Comparison data may be actual data measured from the same bottle during a previous connection, actual data measured from a different but similar bottle or vintage, actual data measured from a different bottle of the same vintage, or a configured set of data representing ideal values for each measured parameter. For example, a set of comparison data may include an ideal temperature value of 60 degrees Fahrenheit for a particular vintage of wine. Comparison data may include ideal values, maximum values, minimum values, or other thresholds for each of the measured parameters, such as a maximum storage temperature, a minimum storage temperature, an ideal storage temperature, a maximum drinking temperature, ideal drinking temperature, minimum drinking temperature, and so on. Once a set of sensor data has been received (302) and a set of comparison data is available (304), the user device (700, 712), or server (710), or both may perform one or more monitoring tasks in serial or in parallel. Monitoring tasks could include a fraud and identity check (306) that could indicate that a bottle has been misidentified or fraudulently labeled, a spoilage check (310) that could indicate a time frame within which a bottle might spoil, a quality check (314) that could indicate whether a bottle is properly aging, or other similar monitoring tasks.

A fraud and identity check (306) could be performed by comparing a bottles measured data to set of comparison data measured from a bottle produced at the same time, by the same producer, with the same contents. For example, if a hundred bottles of wine are produced by the same bottler, using the same contents, and sealed at substantially the same time, any two bottles from the hundred could have one or more parameters measured and compared in order to determine how similar the two bottles were. Measurable parameters such as dissolved oxygen, acetic acid, alcohol content, sugar level, pH level, tannin level, sulfur dioxide levels, phenol content, and other chemical markers should be substantially similar across two bottles produced at the same time with the same contents. If there are substantial differences in the measured data between the two bottles, it may indicate that the measured bottle has been fraudulently labeled and sold or erroneously identified during registration. For example, if a particular batch of wine is known to have an alcohol content of 8%, a comparison data set for that bottle of wine may indicate that 8% is the optimal alcohol content, less than 4% indicates that the bottle may contain something other than wine, and more than 12% may indicate that the user misidentified the bottle upon registration.

If a fraud or identity check (306) indicates that there may be a fraudulent or misidentified batch, the user device (700, 712) may alert the user that a bottle may be incorrectly handled, fraudulent, or misidentified, as well as providing the sensor data and comparison data used to make that determination, so that a user can investigate further. In the case of a fraud or identity alert, the user device (700, 712) may also search for additional comparison data available on the user device (700, 712) or server (710) to attempt to identify (308) the contents of the bottle. For example, in the case that a bottle is measured as having an alcohol content of 12% instead of the optimal 8%, the user device (700, 712) may access the server (710) and query for comparison data where alcohol content is 12%, and one or more other measured parameters also substantially match. If a match is found, the actual identity of the contents of the bottle may be suggested (308) via the user device so that a user may review and make changes to correctly identify the bottle. In some embodiments, comparison data that could be used to identify fraudulent or misidentified bottles may be provided by wine producers and made available via the server (710), allowing a manufacturer to define their own standards and thresholds for authenticity and quality of certain batches of product. Wine producers could even retain control bottles of certain batches of wine that could be stored in ideal conditions and used to provide an ideal set of comparison values for all other bottles produced in the same batch.

A spoilage check (310) could be performed by analyzing measured data from a bottle to determine whether dissolved oxygen, acetic acid levels, pH levels, and other measured parameters for the bottle are within acceptable ranges for wines generally or for a particular batch of wines from which the bottle comes. In addition to comparing a single measurement of these parameters in isolation to an ideal comparison data set, a set of measurements can also be used to identify changes over time. A rise in pH levels or acetic acid levels is a key indicator in the spoilage of wine. As data is collected from a bottle over time and stored on the user device (700, 712), server (710), or both, pH levels and acetic acid levels may be examined for changes from day to day, week to week, or month to month. A sudden rise in pH levels or acetic acid levels from one week to the next may trigger an alert during a spoilage check (310) via the user device (700, 712) so that a user may check the storage conditions and seal conditions of a particular bottle, or choose to sell or consume a bottle before it becomes spoiled. In addition to actively alerting a user as a result of a spoilage check (310), an estimated spoilage date (312) may also be calculated and delivered to a user via the user device (700, 712). By examining changes in pH levels or acetic acid levels over a period of two or more monitoring instances, an estimate can be created for a potential change in pH levels or acetic acid levels over a future week or weeks. When the estimated change in pH level could result in the pH level of a bottle being above a threshold that would indicate spoilage, an alert can be delivered to a user via the user device (700, 712) notifying the user of an estimated spoilage date so that the bottle may be sold or consumed before the estimated data of spoilage.

An overall quality check (314) could be performed periodically to verify that a bottle is properly stored, properly sealed, and predictably aging, as well as to build a set of data over the storage life of a bottle that could be used to verify proper storage, lack of tampering, and predictable aging, and to provide a rich data set that could be used by a collector or consumer to select particular bottles from a collection based upon the particular measurable parameters that they value. The quality check (314) could be a simple data gathering process that would receive sensor data and preserve it on the user device (700, 712), server (710), or both, but could, in varying embodiments, also be a data gathering and scoring process where a score could be assigned to a bottle of wine based upon the measured parameters and the difference between the measured parameters and a set of comparison parameters, or, a scoring process where a score could be assigned to a bottle of wine based upon user configured comparison values. In this manner, a user could select a bottle based upon an abstract or aggregate score representative of an industry standard for quality, or a user configured standard for wine preferred by a particular user.

The quality check (314) could also provide alerts to a user device (700, 712) when a change in measurable parameters indicates that the wine is being improperly stored or quality is unexpectedly degrading. For example, if a present high temperature is detected, or if unforeseen minor changes in temperature are detected, a user may be notified via the user device (700, 712) so that the storage system thermostat or cooling may be inspected. In an embodiment equipped with an accelerometer sensor, any substantial vibrations could be measured and provided as a user device alert, so that the stability of a storage unit could be inspected for nearby causes of vibration. Other changes in measured parameters that might not necessarily be indicative of spoilage, but may indicate some undesirable change in the storage environment or seal, could also cause a notification to a user device (700, 712). Where a quality check (314) indicates that a storage environment is not idea, the system may recommend one or more changes (316) in storage. For example, in an embodiment where a sensor can measure temperature, vibrations, or even lighting, the system may provide an alert to a user device indicating that a particular bottle is being subjected to a higher than ideal level of light, temperature, or vibration. In addition to direct recommendations based upon detected light, temperature, humidity, or vibration, the system may also provide alerts to users where changes in light, temperature, humidity, or vibration might be linked to changes in other measurable parameters. For example, where data measured over time indicates that rising temperatures during noon each day coincide with a relatively high increase in dissolved oxygen, tannin, or other factors in the same time period, the system could provide an alert via the user device (700, 712) that, while the temperature never reaches a high enough level to trigger an alert, a small change each day over a long period of time can negatively impact a bottle.

Figure 4:
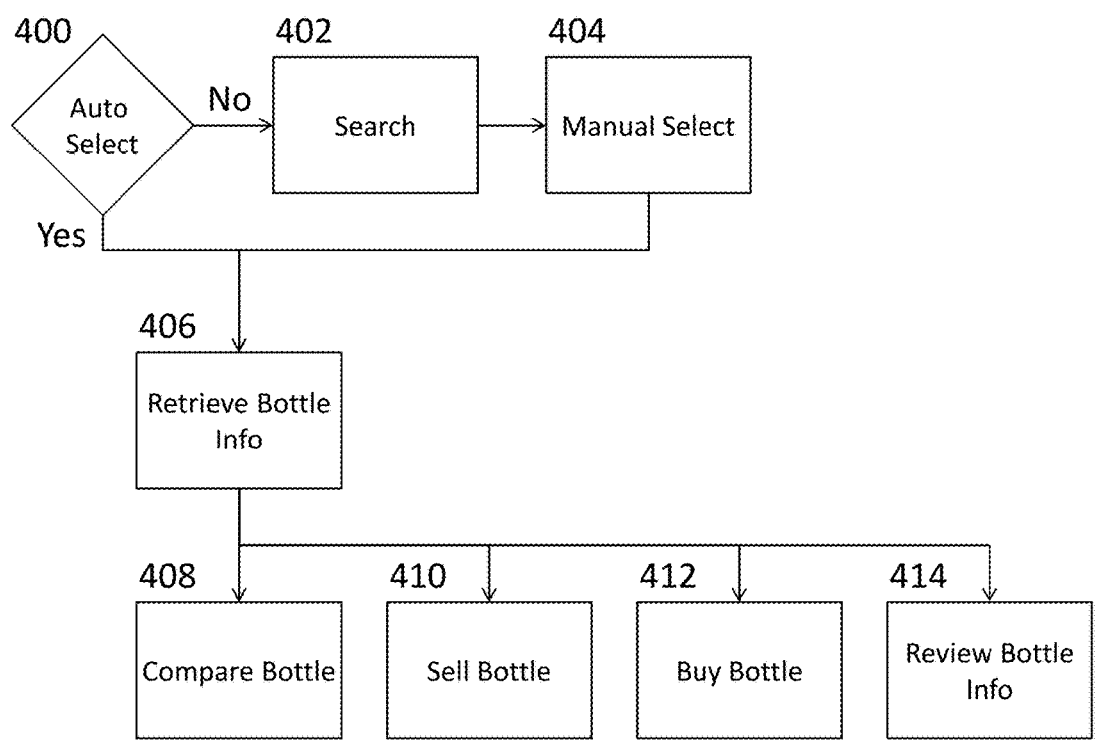
FIG. 4 is a flowchart of a set of exemplary steps that a system could perform to manage one or more sealed containers.

In addition to the monitoring features describe above, the system may also allow a user to manage a collection of registered bottles, as shown in FIG. 4. Via an interface of the user device (700, 712), a user may choose to automatically select (400) a bottle of wine from a collection or manually search (402) and select (404) a bottle of wine from a collection. Automatic selection (400) may identify one or more bottles from a collection based upon collected data, user input or recommended match to a certain type of food. For example, if a user wishes to drink a bottle of wine, interacting with an interface element to cause an automatic selection to occur could select a bottle, based upon estimated spoilage data (312) or data from a quality check (314) that a user should open. In this manner, a user relying on an automatic selection could ideally always open a bottle of wine that is at its peak quality, based upon comparison data of industry norms or user configured preferences for quality, and could ideally always open a bottle of wine before it begins to spoil, based upon an estimated spoilage date (312) calculated from measured pH levels over a period of time. A manual selection may instead be made, by either browsing through a list of each registered bottle via an interface of the user device (700, 712), or by searching (402) for bottles matching one or more user specified criteria. For example, a user could enter, via an interface of the user device (700, 712), desired alcohol content, tannin level, dissolved oxygen, or other attribute. A list of each registered bottle fully or partially matching the searched criteria could be displayed via the interface, a user could manually select (404) a bottle from the list.

When a bottle is selected via the management interface, whether by automatic selection or by manual selection, the bottle info may be retrieved (406) from the user device (700, 712), server (710), or both and displayed for review (414) via the user device. Displayed information could include a bottle name, bottle description, bottle location or storage area, producer, age, or flavor, and could also include a variety of measured parameters such as alcohol content, pH levels, tannin levels, or other parameters. The management interface could also recommend a particular wine in the inventory based on configured recommendations of a match to a certain type of food as specified by the user. In addition to reviewing (414) data on selected bottles, a user may also use a management interface to compare (408) a registered bottle with one or more other bottles, estimate values for and sell or transfer bottles to other users (410), or buy and transfer bottles from other users (412). A comparison of bottles (408) allows a user to select measurement data for one or more bottles from the user device (700, 712), server (710), or both, and display the measured data of the selected bottles as well as the comparison bottles in an interface. In this manner, a user could compare their own bottle of a particular vintage to data from the server (710) on a different bottle of a particular vintage, to determine how their bottle is stored in comparison to other bottles, how their bottle is aging in comparison to other bottles, and other differences.

Estimating values for, buying (410), selling (412), and transferring historic data of bottles could be accomplished by users of the system using a user device (700, 712) in communication with the server (710). When a registered bottle is purchased or appraised, a user could enter the paid price when during registration or after appraisal. Prices could be aggregated by the server (710) over time and would result in a large data set of comparable prices, so that an estimated value of a particular registered bottle might be determined by querying the server (710) for the price of a different bottle from the same batch, or for a comparable value. Users of the system could also buy (410) and sell bottles (412) via the system. In some embodiments, this may involve an interface of the server (710) accessed via a web browser or other software, which could serve as a marketplace for users to post registered bottles for sale, and for other users to purchase a listed bottle. The system provides advantages for such a marketplace, because a bottle listed for sale could be listed along with its estimated value, measured data proving its authenticity and proper storage, measured data describing its various characteristics such as tannins and alcohol level, and other data collected by the system during routine use. When purchasing (412) a bottle through such a marketplace, the historical data gathered by the seller user could be automatically transferred to the user device (700, 712) of the buyer user so that an unbroken history of measured storage and quality data could be retained over multiple transfers. Selling (410) a bottle through such a system could allow the bottle to be automatically unregistered from a seller user's collection, and could automatically generate invoices, shipping labels, and other information relating to the transaction by accessing the buyers information from the server (710). In other embodiments, there may be no marketplace to buy and sell bottles, and instead a user could transfer the recorded data for a registered bottle to another user, with the actual transaction of money and goods occurring outside the system.

FIG. 5 shows a flowchart of a set of exemplary steps that a system could perform to receive data from a sensor while conserving power. Since both integrated sensor bottles and installed sensor bottles require a modular power source in order to allow the sensor to measure data and communicate with a user device (700, 712), conserving power may be important. In order to do so, integrated and installed sensors will be in a lower power state when not in use, and will only be at a full power state occasionally, such as when performing measurement functions. The steps of FIG. 5 show an embodiment where a user device (700, 712) wakes a sensor, but in some embodiments, the sensor may wake itself based upon a predetermined schedule. When a user device (700, 712) wakes a sensor, the desired sensor is first identified (500) via the unique identifier and configured communication method that was established during registration. The identified sensor (500) then receives a signal from the user device (700, 712) causing it to enable (502) its full communication, processing, and sensor capabilities. The sensor may check its power status (504) to determine a battery level, or the availability of a renewable power supply such as a solar power supply, inductive power supply, or other wireless power supply or charger. The system may also take measurements from one or more sensor probes (506) or other sensor devices of the materials, liquids, or gasses that the probes are in contact with, or the physical characteristics of the sensors surrounding environment, such as temperature, vibration, sound, or light. Measured data may be stored by the sensor device for some time while all measurements are taken. Once measurements have been read from the probe (506) they are transmitted (510) via the configured connection to the user device (700, 712). Once the sensor is no longer in active use, the sensor may return to a sleep state (512) where processing capabilities and sensor capabilities are disabled, and where communication capabilities are in a lower power receive only state.

Figure 9:
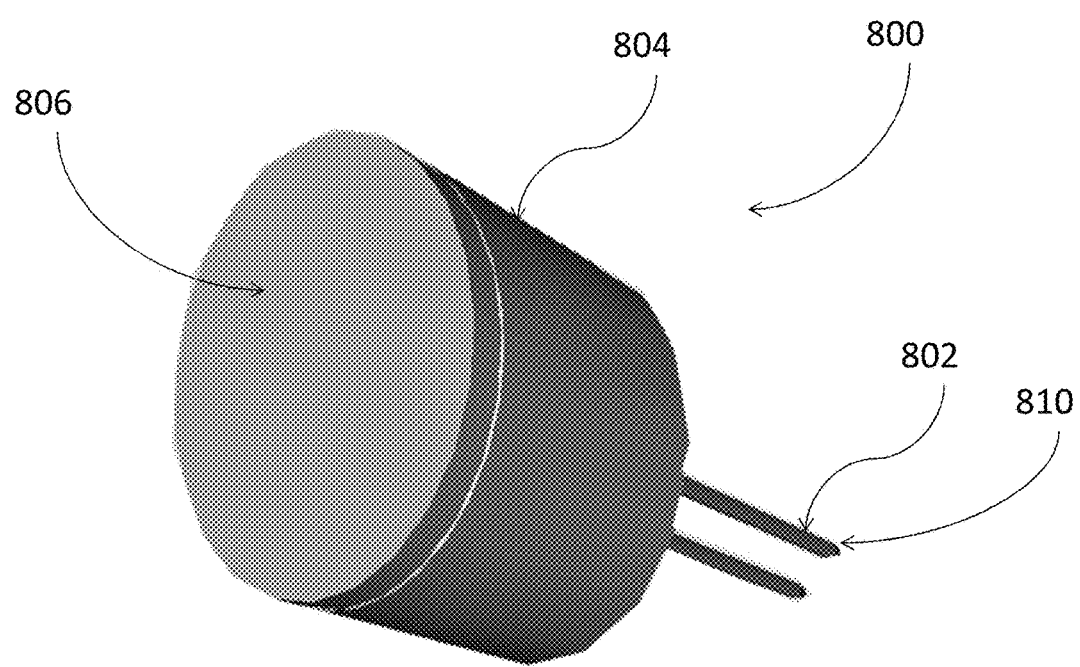
FIG. 9 is a top perspective view of an exemplary sensor device.
Figure 10:
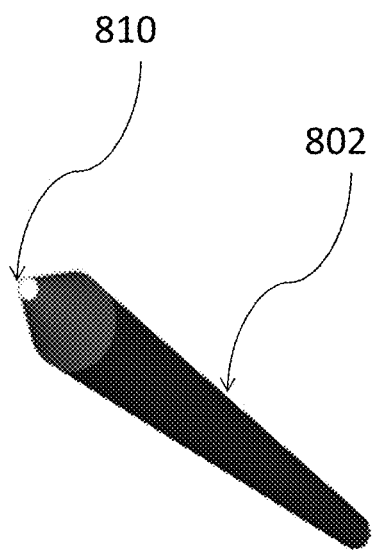
FIG. 10 is a bottom perspective view of an exemplary probe of a sensor device.

FIG. 6 shows a flowchart of a set of exemplary steps that could be performed to install a sensor within a sealed container using unmodified container sealing equipment such as that shown in FIG. 13, an unmodified sealed container, and a SCSD (800) such as that shown in FIGS. 8 and 9. FIGS. 8 and 9 show one embodiment of an SCSD (800) having a casing or body (804) comprising a power source, communication equipment such as Bluetooth or Wi-Fi electronics, processor, memory, and an interface for one or more sensor probes. A removable cap (806) seals the electronics within the casing and gives access to the power supply when removed, allowing easy replacement of a battery or other power source. Two probes (802) extend from the casing (804), with each probe having a sensor tip (810). FIG. 10 shows a zoomed view of the tip of an exemplary micro-sensor probe (802) and tip (810). The micro-sensor tip (810) has a sharpened point configured to pierce through a cork or other seal while displacing a minimal amount of the seal. As shown in FIG. 9, the casing (804) and cap (806) are circular and adapted to fit within unmodified commercially available corking mechanisms. The casing and cap have a diameter that may vary in size by embodiment, but will in most cases be similar or slightly larger to the diameter of the commercially used bottle tops that they are to be used with. Each probe (802) is rigid enough to pierce cork or another sealing membrane without flexing enough to damage or displace the probe (802). Each probe (802) is hollow and allows measurement data to be transferred from a probe tip (810) to a probe interface within the casing (804). The length of the probe will vary be embodiment, but in most cases will be at least the length of the most commonly used cork or sealing membranes. However, a precise length is not necessary, as probes that are longer than the depth of a standard cork or sealing membrane may be installed to any depth necessary even if a gap remains between the top of the cork and the bottom of the casing (804). It should also be appreciated that probe (802) may be attached and removed from the casing (804) to allow for easy replacement of broken probes (802), or to allow for swapping between probes (802) that have different capabilities. For example, one probe may be configured with sensors appropriate to measure several characteristics of oxygen content, while another may be configured with sensors appropriate to measure sugar content. By swapping between these two probe (802) types, a single SCSD (800) may be used to measure multiple sets of characteristics.

Figure 11:
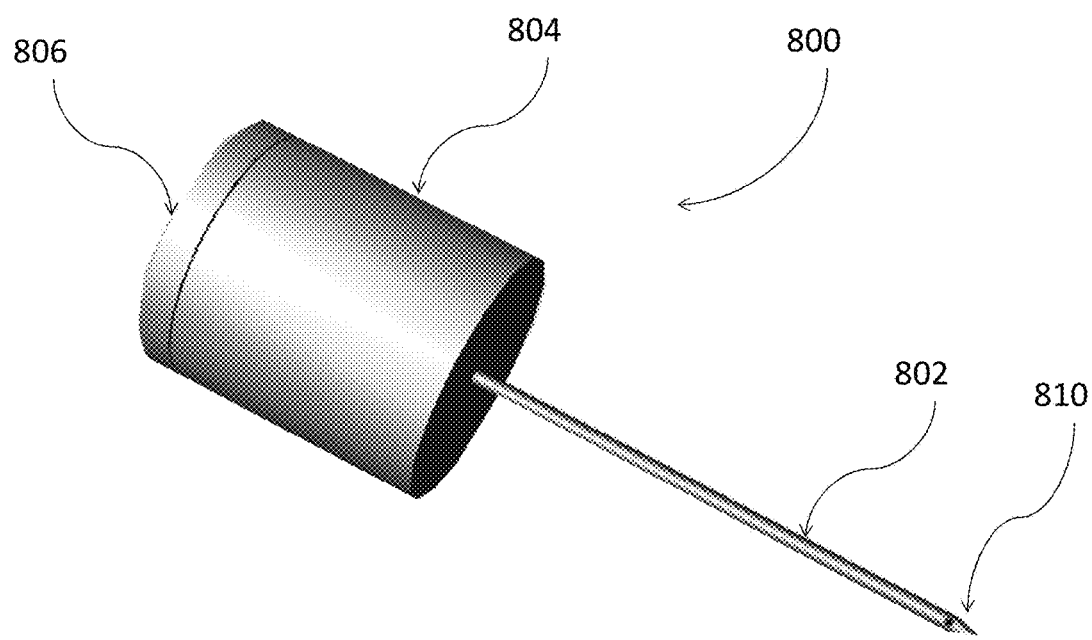
FIG. 11 is a side elevation view of an alternate exemplary sensor device.
Figure 20:
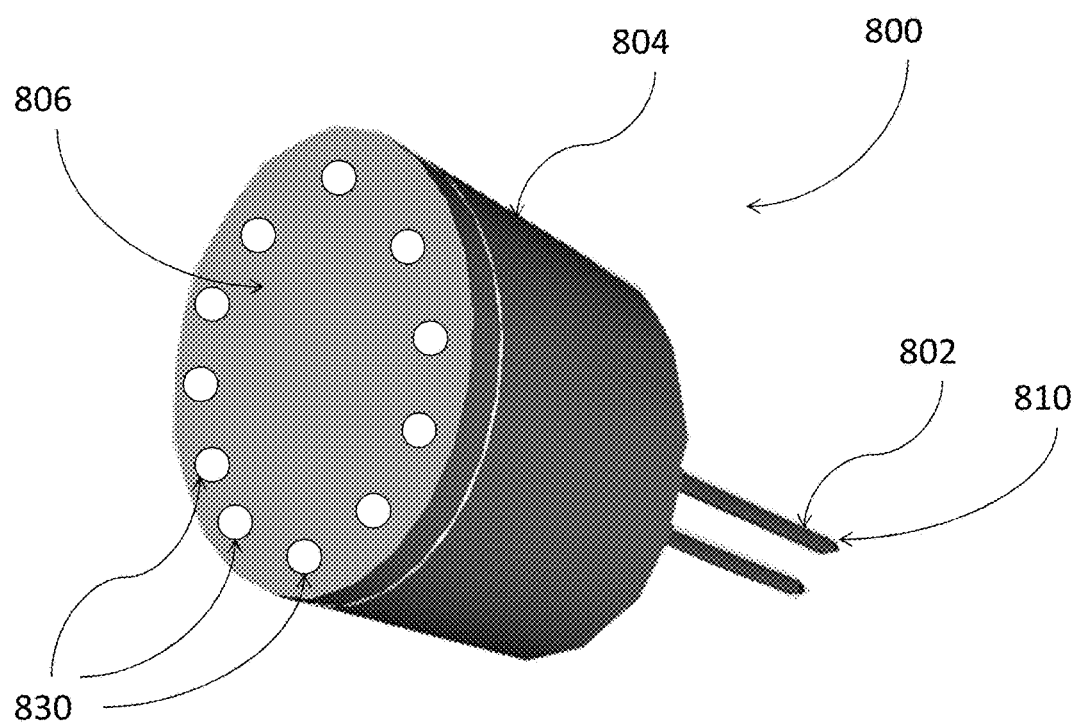
FIG. 20 is a top perspective view of an alternate embodiment of a sensor device.

Each probe (804) and probe tip (810) may contain one or more sensor capabilities, and in some embodiments, the casing (804) itself may contain sensor capabilities. For example, a first probe tip (810) may contain a sensor for measuring pH levels and a sensor for measuring alcohol content, while a second probe tip (810) may contain a sensor for measuring tannins and a sensor for measuring oxygen levels. The casing (804) may contain sensors such as an accelerometer, thermometer, photo eye, or other sensor that does not need to be situated within the sealed container in order to function. FIG. 11 shows an alternate embodiment of an SCSD (800) having a single probe (804) and probe tip (810). A single probe may contain one or more sensor capabilities rather than having the one or more sensor capabilities spread between multiple probes. The number of probes and the distribution of sensors between probes will vary by embodiment. An SCSD with a single probe (804) may be advantageous because it minimizes the displacement of the cork or sealing membrane during installation. An SCSD with multiple probes (804), such as that shown in FIG. 8, may be advantageous because multiple probes may allow for more sensor capabilities, reduced noise between sensors, and additional stability during installation into a cork or sealing membrane. In some embodiments of the SCSD, such as that shown in FIG. 20, removable cap may have one or more light indicators (830) that may be an embedded LED or other lighting source that may be selectively activated for a variety of reasons. For example, in one embodiment the SCSD may be configured to receive a wireless signal that will cause the light indicators (830) to illuminate, flash, cycle, or otherwise activate to assist a user in visually locating a specific bottle from amongst a collection. Alternately, the light indicators (830) may be illuminated in order to indicate the remaining charge for a battery or power source of the SCSD, to indicate an error with the SCSD itself or with the contents of a bottle, to indicate a span of time until which the bottle reaches optimal drinkability or the amount of time that a sensor has been installed on the bottle, or similar functionality. Furthermore, the lights can be used to indicate an approximate value for the measured parameter right on the device by making the whole number solid light and the fraction blinking light for cases where the app is not available or inconvenient to use. In this manner, a value of 3.4 could be represented by lighting a third light indicator with a solid light, and by lighting a fourth indicator light with a blinking light, or by implementing another combination of solid, flashing, pulsing, or intermittent activation of light indicators.

FIGS. 12 and 13 show an exemplary container with an installed SCSD and an unmodified commercially available device that could be used to install and/or remove a SCSD in an unmodified sealed container. In this embodiment, the unmodified sealed container (1200) is a bottle having a neck and mouth sealed with a cork or other membrane. The SCSD (800) is installed at the mouth of the bottle (1200) with the probes (802) piercing through the membrane, holding the SCSD (800) in place, and the probe tips (810) resting either within the pierced membrane, or past the membrane entirely within the body of the bottle (1200). In some cases it may be advantageous to install the SCSD (800) at a depth that the probe tips (810) remain in the cork or sealing membrane, as it may minimize contamination or introduction of cork material into the liquid within. Corks do absorb liquids and gasses that they are contact with, and in many cases will still provide accurate sensor measurements where it is not desirable to pierce through the cork or membrane entirely. This is especially true where bottles are stored horizontally, as is generally recommended and as most bottle storage structures are designed to, as horizontal storage ensures that the cork is in contact with liquids and gasses within the bottle at all times. The unmodified corking device (1300) may be used to install and remove the SCSD (800). The shown unmodified corking device (1300) is exemplary only, as a variety of styles and designs exist, all of which are substantially compatible with the SCSD (800). When the SCSD is removed from a flexible seal such as a cork, the cork itself will return to its original shape as the probes (802) are removed, ensuring that the seal is not compromised.

The SCSD (800) may be placed in the cork seat (1308) with the probes extending downwards towards the bottle seat (1302). If the sensor tips (810) are desired to exit the cork (602), a depth adjustment on the corker (1300) is adjusted so that the corker's maximum downward motion will result in the sensor tips (810) extending beyond the bottom of the cork. If the sensor tips (810) are to remain within the cork (602), the corker (1300) depth adjustment is adjusted so that the corker's maximum downward motion will allow the sensor tip (810) to come as close to extending beyond the bottom of the cork as the user desires without piercing through. An unmodified bottle (1200) may be placed (608) in the bottle seat (1302), and the handle (1306) actuated to cause the corker applicator (1304) to push the SCSD (800) downwards, guided by the cork seat (1308) so that the probe tips (810) pierce the cork and the SCSD becomes securely seated atop the unmodified bottle (1200) with the probe tips (810) extending just past the cork, or, remaining just within the cork. The unmodified corking device of FIG. 13 could be used to remove SCSD from the bottle, for instance, before opening the bottle and consuming the wine, when selling the bottle, or when monitoring is otherwise no longer desired. This same SCSD could then be used on a different sealed wine bottle. When uninstalling the SCSD, the cork seat (1308) may be used to grip the SCSD while downward force is applied to the unmodified bottle (1200). Commercially available corkers may also be useful in installing and uninstalling the SCSD (800) when lightly modified. For example, a bottle seat (1302) that could grip a bottle, such as by a flexible rubber clamp or vise, could be used to aid in the application of downward force, ensuring that the SCSD (800) is removed in a linear manner without slippage or horizontal displacement.

III. Exemplary Sensor Integrated Bottle

Figure 14:
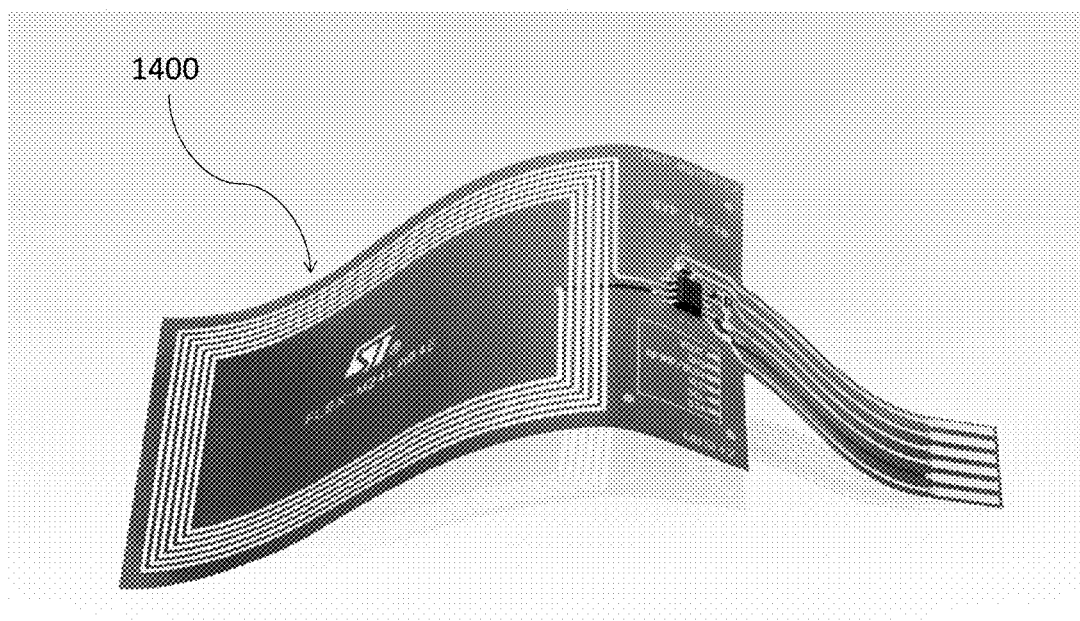
FIG. 14 is a top perspective view of an exemplary flexible circuit.
Figure 15:
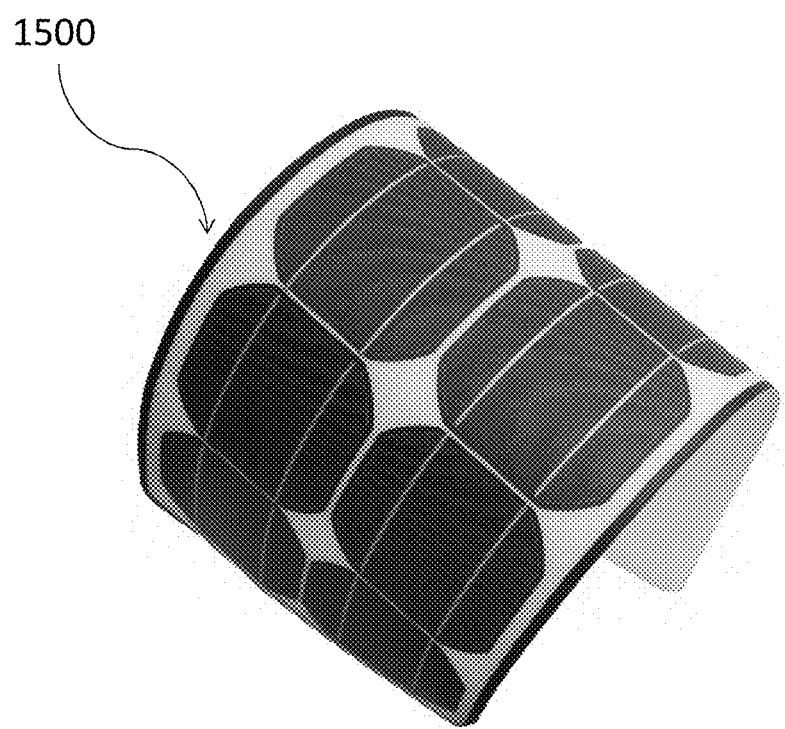
FIG. 15 is a top perspective view of an exemplary flexible solar power source.
Figure 16:
FIG. 16 is a side elevation view of an alternate exemplary sensor-enabled container.

FIGS. 14-16 show components of an integrated sensor bottle (702). A flexible circuit (1400) houses processing capabilities, memory, communication capabilities, and sensor interfaces in a flexible package that can be placed under a label or foil wrap (1602) of an integrated bottle (1600) at the time of bottling. The flexible circuit (1400) is able to conform to the surface of the bottle and provides the full capabilities of the SCSD (800) while being fully or partially concealed beneath a wrapper or other normal bottle design element. A flexible solar power source (1500) could also be applied to the bottle at the time of manufacture, and may be integrated with the bottles design or labeling in such a way that it is exposed to surrounding light sources and connected to the flexible circuit (1400). The sensors of an integrated sensor bottle (702) may pass through a sidewall of the integrated bottle (1600) via a sealed passage left in the bottle during manufacture, or could exit the foil wrap (1602) at the mouth of the bottle and be present within the cork at the time of installation. The integrated sensor bottle (702) would function similarly to the SCSD (800), but would draw power from renewable sources, such as the solar power supply, rather than a modular or replaceable power source. In this manner, a light may turn on within a wine storage unit once per day, causing all the integrated sensor bottles (702) therein to wake and transmit sensor measurements to a user device (700, 712) or server (710), then to return to a sleep state when the light turns off. In another embodiment of the system, Lithium batteries could be integrated in a cap, on an external portion of the bottle, embedded in the structure of bottle, or within a decorative label or seal as backup power in cases where there is not enough light to create power by the solar cells. In yet another embodiment, a combination of a Lithium battery as a primary power source and a solar cell as a secondary power source or as a way to recharge a Lithium battery could be used to provide even more versatile configurations.

While previous discussions have disclosed using a modular sensor or sensor integrated bottle on everything from a bottle of wine, to a single grape, to a batch of grape must, it should be understood that such a sensor could be used on a variety of liquids, gases, or other substances. For example, in some embodiments, a sensor or sensor enabled container could be used to track the condition of and, in effect, the efficacy of medicines. Medicine expiration dates are somewhat arbitrary dates that are determined based upon estimated degradation of active ingredients based upon average conditions such as temperature, humidity, sunlight, and other factors. Because of this, medicines stored in extreme temperatures may lose their efficacy before an estimated expiration date, while in other situations medicines stored in ideal conditions may be disposed after their expiration date while still having an effective shelf life. Since end users of medicine have no meaningful way to determine the efficacy of a medicine beyond its listed expiration date, there is a potential both for users to rely on a medicine that should be disposed of or replaced, as well as a potential for users to dispose of medicine that could still be put to good use. This impact is especially costly in areas and settings where medicine availability is low, and may have a disparate impact in areas such as third world countries and other areas where access to simple medicines such as pain relievers, antibiotics, and immunizations can be the difference between life and death.

Use of a sensor integrated bottle or modular sensor with liquid medicines and vaccines could allow for micro-sensors to track storage conditions during the life of a medicine and calculate expiration dates in real time based upon actual storage conditions rather than manufacturer estimated storage conditions. By tracking and gathering sensor data over time to store on a memory device integrated with the sensor, such characteristics as temperature, humidity, exposure to sunlight, and other characteristics related to storage, packaging, and transit can be determined at any single time during the life of the bottle. Thus, if a certain medicine is known to be ineffective if temperature exceeds a certain level, several weeks or months of data can be examined to determine if the temperature of the medicine ever exceeded the known threshold for ineffectiveness. The ability to store long term data on the sensor memory itself, as well as transport that data to a user device or remote server, allows the sensor device to be configured to balance between an offline operation where data is stored locally on a long term storage medium to conserve power consumed by wireless transmission, and an online operation where data is transmitted to external sources in order to conserve local storage. This could meaningfully decrease reliance on ineffective medicines as well as disposal of still effective medicines. In some embodiments, micro-sensors could also be used to detect either the concentration of active ingredients, or the concentration of substances created as a byproduct of the degradation of active ingredients. With such a micro-sensor placed into a liquid medicine or integrated with a smart medicine bottle, the actual concentration of active ingredients could be measured or estimated based upon byproducts and could be used to determine whether the active ingredients are still above a usable threshold at any given time. Other such examples exist both within the field of medicine and pharmaceuticals as well as other fields where on demand measurement of characteristics of liquids or gases may be valuable, and will be apparent to those of ordinary skill in the art in light of the disclosure herein.

IV. Exemplary Interface for Monitoring and Management of Sealed Containers

Figure 17:
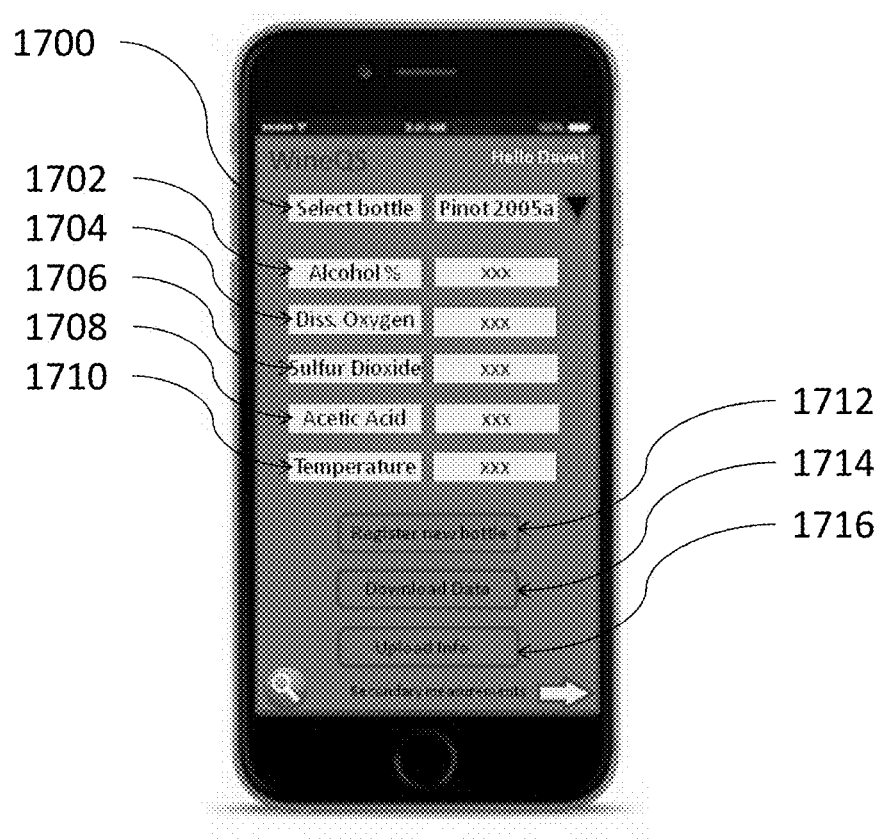
FIG. 17 is an exemplary interface that could be used to interact with a sensor device and other systems.
Figure 18:
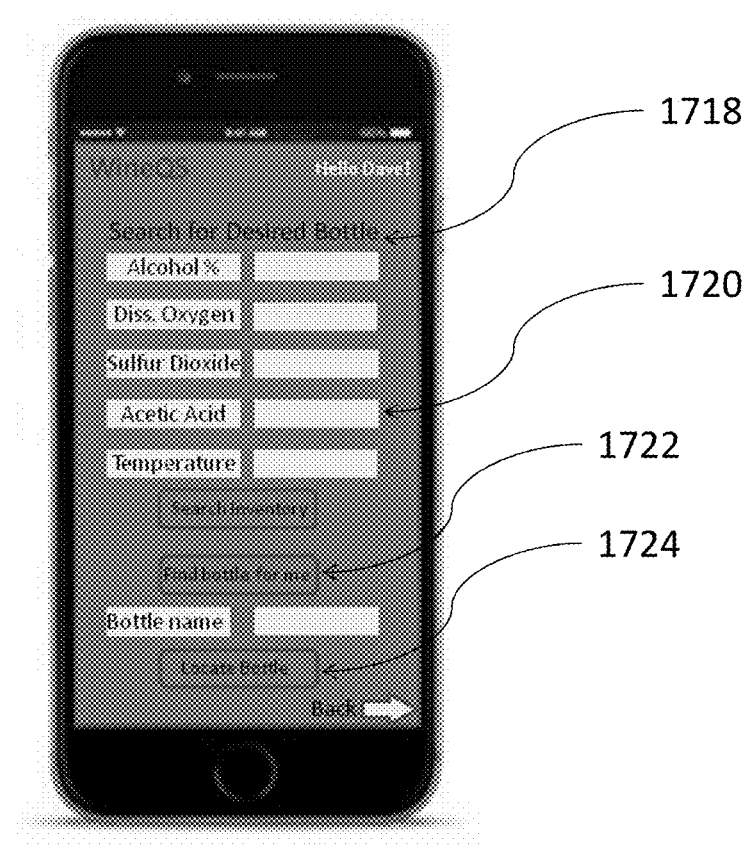
FIG. 18 is an exemplary interface that could be used for further interactions with a sensor device and other systems.

FIGS. 17 and 18 show an exemplary interface that could be used via a user device (700, 712) to manage, query, and monitor a collection of registered bottles. Using the interface, a user could select (1700) and search (1718, 1720) for bottles, automatically suggest bottles (1722), physically locate (1724) a bottle within their storage area, could review measured parameters of bottles such as alcohol content (1702), oxygen (1704), sulfur dioxide (1706), acetic acid (1708), and temperature (1710), and could register new bottles (1712), share measured data with another device (1714) or upload data to a server (710) for backup and aggregation with other user data. For example, the user may decide to download all the data for the entire inventory to a single file for collective viewing and comparison. Other exemplary data that may be shown when monitoring bottles may include dissolved oxygen content, sugar content, pH measurements, titrate acidity, phenol measurements, time and date values indicating a time that the displayed data was collected or measured at, or other data that may desirably be gathered and displayed.

Further variations on, features for, and applications of the inventor's technology will be apparent to, and could be practiced without undue experimentation by, those of ordinary skill in the art in light of this disclosure. Accordingly, the protection accorded by this document, or by any related document, should not be limited to the material explicitly disclosed herein.

V. Factors Influencing Configuration of Comparison Values and Monitoring

Numerous factors will influence the configuration of monitoring capabilities and the availability and selection of comparison data (304) that is used during monitoring tasks. Such factors will vary by embodiment, by the particular container and contents being monitored, and by a particular user's preference. A discussion of some factors that could influence comparison value choice and monitoring of sealed containers of wine follows.

A variety of grapes are used to make the most popular wines, either singly or in combination with one another. This gives rise to an incredible number of possible chemical mixture compositions from one type of wine to another. The chemistry of wine can be complex. Many factors influence the final wine product including the type of grape, age of the grapes, the growing conditions, and harvest method. As grapes ripen, their acid level usually declines while sugar, color, and tannin levels increase. A wine's need for acidity should be balanced with the desire for richness gained from ripeness. Ideally, acid, alcohol, fruit, and tannins should be balanced. Insufficient acidity makes a wine dull, whereas excessive acidity makes the wine sharp and raw tasting. An excess of tannins usually makes a wine bitter, but the right amount of both acidity and tannins produces a wine that is refreshing and has a flavor that lingers. Thus, spoilage of wine is associated with oxidative mechanisms, weight refers to the alcohol content of the wine, and body refers to the mixture of fruitiness and alcohol (i.e., the feel of it in the mouth). A "well-bodied" wine is alcoholic and fruity, and white wine is crisp with low alcohol content.

There are numerous external chemicals that may be added to wines, and which could serve as measurable indicators of a wine's quality. For example, sulfur dioxide ($SO_2$) may be added to control oxidation and kill unwanted bacteria, and Sorbic acid may be added to inhibit the growth of yeast and bacteria in sweet wines. It may be important to measure the sulfur dioxide concentration to determine wine age and quality. It may also be important to monitor phenol content, as the wine will take on a bad odor if ethyl phenol or vinyl phenols are present. Furthermore, many wines are clarified (fined) using agents such as egg whites, gelatin, isinglass (protein from fish), liquid tannin, charcoal, and certain clays.

The fermentation process for wine usually takes place in two parts. The first part is usually conducted in the presence of air and is aerobic. Fermentation conducted in the absence of air is generally the second portion of the process. Wine can turn to vinegar when vinegar bacteria are allowed access to the wine. Infected equipment, fruit or the vinegar fly may cause the wine to turn. A fermentation trap or airlock may be employed to protect the ferment. The fermentation trap will let gas pressure escape but admit no air. The fermentation trap can also be used to cut off the air supply and force the yeast to turn to a secondary method of self-reproduction without oxygen, which is appreciably more productive of alcohol. During the fermentation process, yeast must have sugar, warmth, oxygen, and a certain amount of nitrogenous matter, vitamins and acid. If the recipe does not provide all of these or even if any one of them is lacking, the ferment may stick, or temporarily stop. Due to the varying importance of certain measurable parameters at different stages of wine production and storage, a selection of comparison values immediately after sealing during a fermentation period may differ from comparison values selected some years later during storage.

The process of forming wine in casks or vats is extremely specific. Occasionally, a third fermentation occurs. This usually happens a year or more after the wine has been bottled. The optimum pH level for wine during this period is usually 3.2 but may vary from 3.0 to 3.4. The low acidity prevents the production of many chemical species associated with wine spoilage and the growth of microorganisms. Thus, one of the earliest and most sensitive indicators of wine spoilage or impending spoilage is the rise in pH level. Increased pH reduces the stability of the anthocyanin pigments and leads to early loss of color. Coupled with spectroscopic analysis of color, pH changes should increase the sensitivity of the measurements for determining aging or spoiling of the wine. The effect of aging wine in the bottle is associated with a color shift from red to brown. Red wines initially deepen in color after fermentation but later take on a lighter ruby, then a reddish-brown, hue. Decreased color intensity and browning result from a disassociation of anthocyanin complexes and the progressive formation of anthocyanin-tannin polymers. Given the number of different factors influencing wine quality, it is clear that the particular comparison values and target values used during monitoring tasks will vary be embodiment and application, with such variations being apparent in light of this disclosure.

VI. Exemplary Probe and Sensor Design

Figure 19:
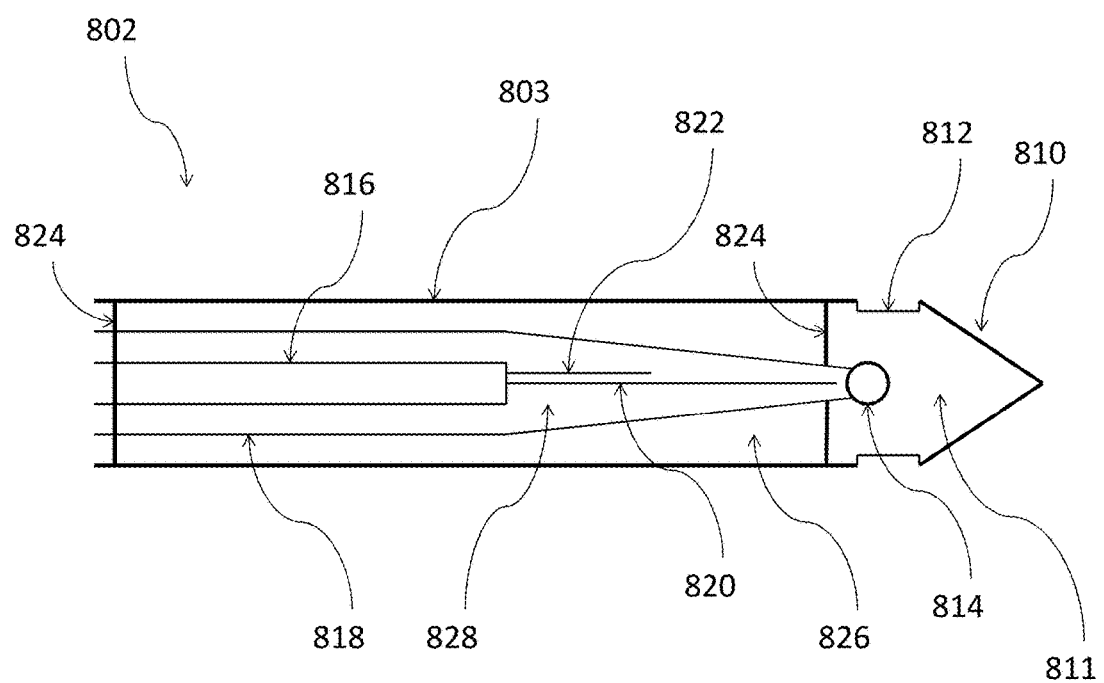
FIG. 19 is a cross section view of an example of a probe needle.

FIG. 19 shows a cross section view of one example of a needle probe and sensor design for a probe (802) of a SCSD. In the shown embodiment, probe (802) exterior case (803) may be made of a rigid and durable material such as a metal, plastic, tempered glass, or other material that will allow the probe (802) to pierce a variety of membranes while minimizing flex in order to protect embedded components. The probe tip (810) may have a blade or needlelike edge to aid in penetration, and may additionally have one or more tip openings (812) to allow liquids, solids, and gases to enter and pass through a tip chamber (811) after probe tip (810) pierces a sealed container membrane. Tip chamber may have one or more sensor membranes (814) that come into contact with substances that pass through tip chamber (811). The sensor membrane (814) may be a porous or perforated material that allows small portions of substances that come into contact with the sealed container membrane (814) to pass into an inner sensor cylinder (818). The inner sensor cylinder (818) may be a rigid tube, cylinder, or other shape made of glass, plastics, metals, or other rigid substance that will protected embedded components. The inner sensor cylinder (818) may be filled with a liquid, such as an electrolyte solution (828) to provide a predictable and controllable area where portions of substances that pass through the sealed container membrane (814) may mix and float.

Substances floating within the electrolyte solution (828) may come into contact with or be detected by a measuring sensor (820) and a reference electrode (822). Measuring sensor (820) and reference electrode (822) extend outward from a sensor wire cylinder (816) toward the sealed container membrane (814). Sensor wire cylinder (816) protects the encased measuring sensor (820) and reference electrode (822) and runs the length of the probe (802) so that measurements gathered by the sensors may be passed from the tip chamber (811) back to the processor and memory contained in the housing (804). Each end of probe (802) has a probe seal (824) that extends from exterior case (803) and seals around the inner sensor cylinder, creating an inner vacuum (826) around the inner sensor cylinder (818). Probe seal (824) may be a plastic, rubber, epoxy, or similar non-contaminant substance that may be applied after inner sensor cylinder (818) is in place to both hold the inner sensor cylinder (818) in place and to preserve the inner vacuum (826). In some embodiments, the inner sensor cylinder (818) may be removed from the probe (802) and replaced with a new inner sensor cylinder (818) if the electrolyte solution (828) becomes contaminated or if a sensor becomes faulty. A new inner sensor cylinder (818) may be inserted into the probe (802) after an old cylinder is removed, and new probe seals (824) may be placed at each end of the new inner sensor cylinder (818). In addition to affixing the inner sensor cylinder (818) in place, the probe seals (824) may also provide protection against vibration and other forces for the delicate sensors, creates a vacuum within the exterior case (803) to reduce the possibility of oxygen or other gases being passed into a sealed container, reduces the amount of wine that must pass into the tip chamber (811) for measurement purposes, and other advantages.

VII. Exemplary Methods of Manufacture for Probe

Figure 21:
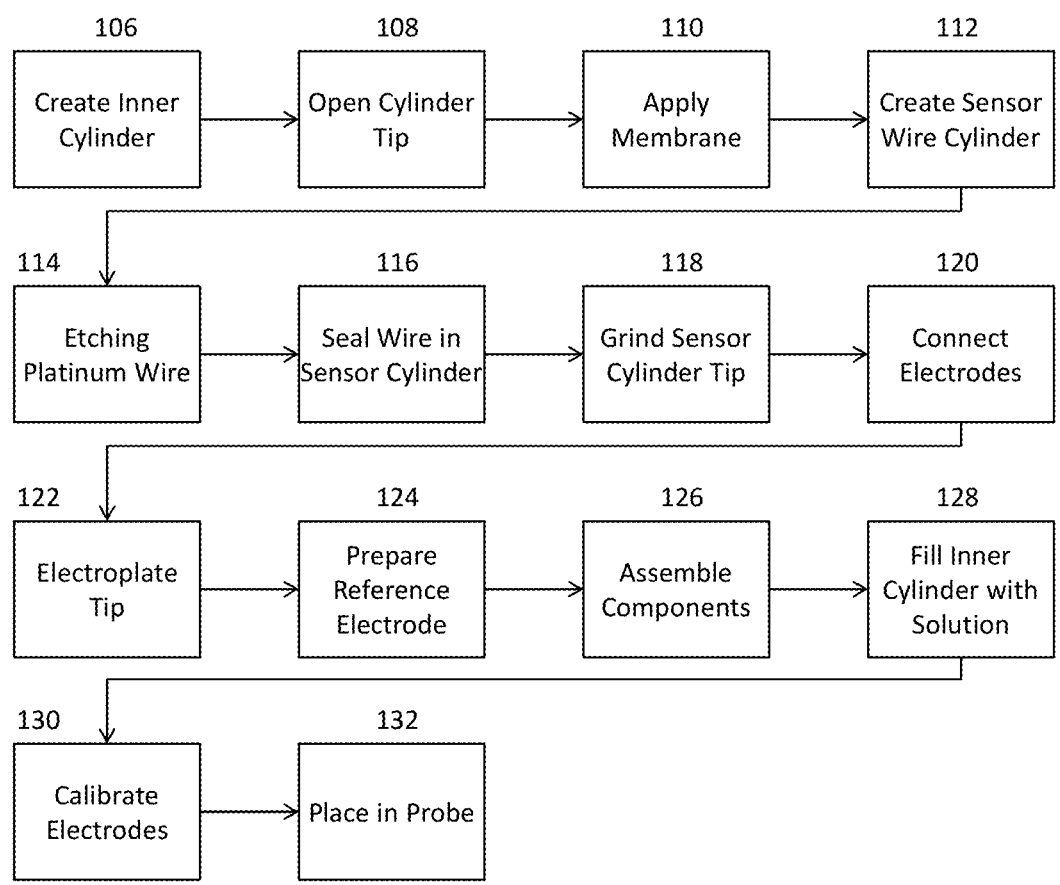
FIG. 21 is a flowchart showing an example of a set of steps that may be performed to manufacture a sensor for measuring oxygen characteristics.

Assembly of a sensor probe may vary based upon the characteristics that the sensor is intended to measure. FIG. 21 shows an example of a set of steps that may be performed to manufacture a probe with a sensor configured to detect dissolved oxygen. While these steps largely apply to creating components of the probe from glass, any suitable material may be used, such as plastic or metal, and some of these principles may apply in addition to using molds, machining, or other methods of manufacture specific to those materials. First, the inner cylinder is created (106). A commercially available capillary, such as a Harvard apparatus 30-0089 capillary, may be used as a starting point. The dimensions of the Harvard apparatus 30-0089 capillaries are 1.2 mm (OD)×0.93 mm (ID)×100 mm (L) and it can fit into commercially available exterior cases (803). The prepared capillary is used as the inner sensor cylinder (818) of the dissolved oxygen microelectrode (DOM). The capillary is pulled in three-steps to achieve a 10-20 µm tip diameter (836). The capillary may be pulled by hand or by machine while heat is applied. The capillary is held by one of the ends over the flame and rotated. The reason for holding the glass capillary near to one of the ends is need of a ~10 cm inner sensor cylinder (818) with its pulled tip. Because, the length of commercially available exterior cases (803) is 9.15 cm and long outer case is needed to reach near the tip openings (812) to be in contact with substances entering the tip chamber (811). As the capillary is heated it becomes soft. When it is sufficiently soft, it may be pulled apart by hand or by a machine (832). The force of the pull should be substantially straight so that the capillary linking the ends does not bend. The flame may be used to break the capillary from the middle of thin melted part (834). The long piece will be the inner sensor cylinder (818) of the DOM. The prepared pieces should be kept in a clean/dust free location until assembly in order to prevent contamination.

Pulling the capillary may be accomplished in different ways. In one process, the thin end of the inner sensor cylinder (818) is put through the heating element shaped in the form of a loop and attached to the micromanipulator using the alligator clip. The micromanipulator is positioned above the heating element and attached to the micropipette puller. The glass shaft will be pulled using heat from the heating element and gravity, and some weight may be added to the shaft to increase the level of control over this process. The pipette is lowered to the desired position to start the necking down of the pipette. The location of the correct position is somewhat arbitrary, but it should be close to the tapered region so that the first tapered part—the one generated by pulling the capillary by hand—becomes a part of the second tapered region. Ideally, the two tapered zones should have a smooth transition. The capillary will slide down somewhat, but not too far, just enough to make the tip diameter smaller than what you had after drawing the capillary by hand. The tip diameter will still be large; it will be reduced by the next stage of pulling. At each stage of pulling, the precision needed increases.

For example, the first pull is easily performed by hand, the second pull may be more easily accomplished with a process as described above, and the third pull may best be accomplished by using a heating element made of a 100-µm Pt wire, which can heat a very small surface of the glass at a precisely selected location. For the third pull, the tapered part of the micropipette may be positioned in the field of view of a stereomicroscope. The pipette may be repositioned so that the heated spot is now next to the heating element. Using a thinner heating element, made of 100-µm Pt wire, the current is increased through the heating element until it is glowing red. When the glass begins to melt and the pipette begins to drop, the current to the heating element may be turned off. Controlling the heat source is the key to this procedure. It may be helpful to turn the heat on and off during melting to control the heat. If too much heat is applied, the capillary will melt completely through and fall down. A heating element device is used for necking down the outer case. Repeat the above procedure, by stopping the current flow through the heating element when the pipette begins to drop. Reposition the pipette so that the heating element is near the thin part and repeat the previous steps of the procedure. Two applications of this procedure should sufficiently taper the inner sensor cylinder (818). However, results may vary, so keep repeating this step until the tip diameter of capillary is less than a few micrometers. The capillary inner sensor cylinder (818) can be allowed to drop after the taper is sufficiently thin. While the above describes a largely manual process, the creation of the inner sensor cylinder (818) could be largely automated.

Figure 24:
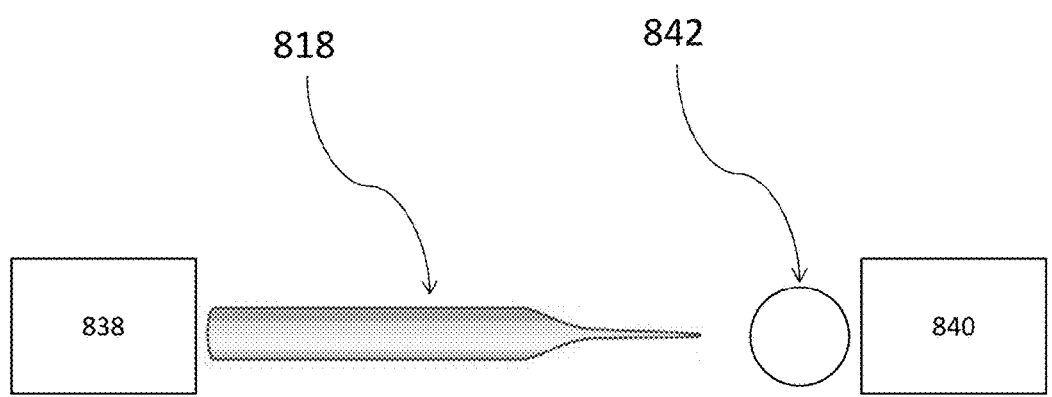
FIG. 24 shows a glass ball being used to break the tip off a glass cylinder during a stage of manufacture.
Figure 25:
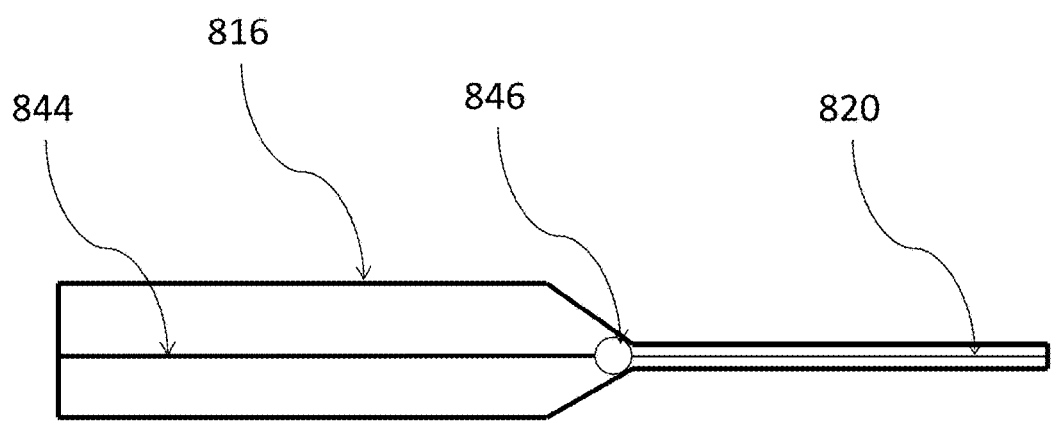
FIG. 25 shows a wire being connected to a sealed and etched wire within a glass cylinder during a stage of manufacture.

Next, the inner sensor cylinder (818) tip may be opened (108), since the tip is likely sealed due to the tapering described above. Therefore it is necessary to open the tip and expose the inner part of the inner sensor cylinder (818). This can be accomplished by hand using a glass rod with a ball and then pushing the tapered end of the inner sensor cylinder (818) against glass ball under a microscope. FIG. 24 shows a fastener (838) holding the inner sensor cylinder (818) and micromanipulator (840) which is adjustable to push glass ball (842) against inner sensor cylinder (818). The microscope may be focused on the capillary inner sensor cylinder (818) and brought into focus using the 10× objective (total of 100× magnification) on the microscope. The stage is moved far enough so that the fragile tip of the inner sensor cylinder is out of the way. Using the micromanipulator (840), the glass ball (842) is moved under the microscope and brought into focus (the end of the ball should be visible in the microscope's field of view, but not take up more than half of the field of view). The inner sensor cylinder (818) is then brought back into focus. The two objects are then both in focus. It may be useful to move the micromanipulator until the glass ball comes into focus while the tip of the outer case remains in focus. Having both objects in focus ensures that they are at the same level under the microscope. The inner sensor cylinder (818) may be backed up a little and jammed into the glass ball (842). Make sure this is done lightly, so the capillary casing does not break lower down the capillary outer case, past the 10-μm width. Keep jamming the inner sensor cylinder (818) into the ball (842) until the end of the casing is 10 μm in diameter. As with other steps, while breaking the tip has been described as being performed by hand above, it may also be automated.

Next, a membrane may be applied (110) to the opened tip of the inner sensor cylinder (818). This may be performed using the glass ball (842) of FIG. 24. A tiny drop of silicone rubber may be placed on the end of the glass ball (842) which contacts the open tip when they are moved together. The glass ball (842) and open tip may again be brought into focus, and the inner sensor cylinder (818) may be slowly advanced towards the rubber on the glass ball (842). The open tip may be inserted into the silicone rubber, and through capillary action, the silicone rubber may advance up the outer wall of the inner sensor cylinder (818) until it is approximately 10 μm thick at the tip. The inner sensor cylinder (818) may then be backed away from the glass ball (842) and set aside to dry, at which point the inner sensor cylinder is complete.

Next, a sensor wire cylinder (816) may be created (112). The shafts of the microelectrodes may be tapered to a tip diameter of several hundred micrometers. This tapering is done in a few steps. At first, this may be done by hand, similarly to the process described in creating the inner sensor cylinder (818). A slightly smaller diameter of cylinder is used, for example, Corning 8161, which may be pulled longer at least 10 cm. Because, this sensor wire cylinder (816) should be able to fit into the inner sensor cylinder (818) (with ID=0.93 mm) constructed in the previous step. The thin part of the pulled glass will be 10 cm and Pt wire will be etched in the next step will be placed into this part. Use the edge of the file to score the glass, and break the capillary in the middle. These pieces may then be set aside in a dust free and clean storage until assembly.

Next, a platinum wire may be etched (114) for use with the measuring sensor (820) and reference electrode (822). Pt wires may be etched electrochemically in concentrated potassium cyanide, KCN. KCN solution is prepared in scintillation vials by dissolving 8 g cyanide KCN in 30 mL of DI water. After the chemicals dissolve, the counter electrode may be inserted. The counter electrode may be, for example, a graphite rod (Aldrich 4965405, 3 mm diameter). Either 50 or 100 μm thick Pt wire may be used for etching. The wire may be cut into sections of at least 10 cm, depending upon the length of the inner sensor cylinder (818) and overall length of the probe (802), but 10 cm may fit many commercially available probe casings (803). The wire may be washed with DI water and attached to a terminal of AC voltage source, then submerged about 1 cm into the cyanide solution. The voltage may then be increased to about 2-8V, which will cause the Pt wire to bubble. This will taper the wire and allow the tapered end to fit into the tapered part of the sensor wire cylinder (816). The wire may be tapered to about 10 μm. The wire may then be cleaned and set aside for later assembly.

Next, the etched wire (820, 822) may be sealed in the sensor wire cylinder (816) so that only the etched tip is exposed. This should be performed carefully so that neither the wire nor the sensor wire cylinder (816) is damaged. The wire sensor cylinder (816) may then be heated to seal the etched wire inside tightly, without air bubbles, dirt or debris between the inner wall of the sensor wire cylinder (816) and the etched wire (820, 822). The sensor wire cylinder (816) tip may then be ground (118) to ensure that the etched wire (820) contained inside is exposed and clear of defects. Using a micromanipulator and a grinding wheel suitable for use with microelectrodes, the tip of the sensor wire cylinder (816) should be ground down until the edge of the tip and the etched wire (820) are flush with each other and the tip is flat and has an exposed diameter of about 10 μm. The etched wire (820, 822) may then be connected to external circuitry (120), as shown in FIG. 24. A less fragile external wire (844) may be placed inside sensor wire cylinder (816) and connected to etched wire (820) by a conductive connection (846) may by solder, a jumper, a bus, or any other suitable connector type. External wire (844) travels the length of the sensor wire cylinder (816) and probe (802) and allows data gathered by the etched wire (820) to travel the length of the probe and be received by a processor and memory in the housing (804).

The etched wire (820) tip may also be electroplated with a conductive and protective coating (122) such as gold. Electroplating the etched wire (820) tip with gold makes the electrode resistant to contamination and corrosion, especially from hydrogen sulfide which may be present in anaerobic biofilm, and which may penetrate the membrane (814) and contaminate the etched wire (820) tip. Two examples of compounds that may be used to electroplate the etched wire (820) tip include $HAuCl_4$ and $KAu(CN)_2$. $HAuCl_4 \cdot 3H_2O$ (Sigma, #G-4022) may in some cases be preferable because it has better solubility and produces a more porous gold tip with a larger surface area, which results in a very stable signal. The selected compound may be mixed into a solution and coating the tip via capillary forces. Electric may then be supplied causing the compound to plate the tip in a spherical shape of 5-15 5-15 μm in diameter.

The reference electrode may also be prepared (124). The reference electrode is not really a reference electrode, but is actually a counter electrode. The counter electrode reaction delivers the electrons to reduce oxygen to water at the tip of the cathodic part of the sensor. However, because the counter electrodes used in oxygen sensors are typically the electrodes that are used as the reference electrodes in potentiometry, the name reference electrode is commonly used for the counter electrodes used in amperometric sensors. In principle, dissolved oxygen electrodes can be operated with external or internal reference electrodes by using internal reference electrodes placed inside the sensor wire cylinder (816) of the microelectrodes. The position of the reference electrode—inside sensor wire cylinder (816) or outside it—is not only a matter of cosmetics or the elegance of the design: it affects the performance of the electrode. Specifically, inserting the reference electrode into the inner sensor cylinder (818) decreases the level of electromagnetic noise experienced during measurements. All our dissolved oxygen electrodes are constructed with internal reference electrodes.

A piece of silver wire may be cut, about 0.1 mm in diameter and 3-5 cm long. The wire should be long enough to reach about three quarters of the way down the inner sensor cylinder (818) and stick out the back of the electrode. The silver wire can then be connected to a power supply and close the circuit with a graphite rod. The silver wire and carbon rod may then be placed into a solution, such as a 0.1 M HCL solution, and increasing the voltage for about 90 minutes. A lower voltage for a longer period of time produces a smoother layer of AgCl on the silver wire. After chlorinization, the electrode may be aged for 1-2 days in dilute HCl (0.1 M) to stabilize the electrode potential.

At this point, the components may be partially assembled (126). The sensor wire cylinder (816) may then be carefully inserted into the inner sensor cylinder (818) until the etched wire (820) tip is about 10 μm from the membrane (814). The probe seal may then be placed or injected in a liquid or flexible form which later cures and becomes a complete and semi-permanent seal. The reference electrode may then be inserted into the sensor wire cylinder (816) or inner sensor cylinder (818), depending upon the embodiment, and attached to the inner wall of its container with an epoxy, glue, or other fastener. The inner sensor cylinder (818) may then be filled with a solution such as an electrolyte (128). One solution that may be used is 0.3 M $K_2CO_3$ (41.46 g/L), 0.2 M $KHCO_3$ (20.02 g/L) adjusted to pH 10.3, and 1 M KCl (74.55 g/L) as the internal electrolyte for oxygen microelectrodes. A reasonable compromise between a relatively high pH and tolerable decomposition rates of micro-sensor components is obtained at a pH of 10.3. A sonicator may be used to remove air bubbles from the solution if necessary to remove them. A syringe may be used to fill the tip of the inner sensor cylinder (818) with solution, as it is only a few nm in diameter. The inner sensor cylinder (818) should be filled from a point close to the tip, and a vacuum may be used to remove any air bubbles remaining in the tip. After the tip is filled with solution, the rest of the inner sensor cylinder (816) may be filled with solution and the unsealed end of the cylinder may be sealed with a probe seal (824).

After the cylinder has been filled with solution, the electrodes may be calibrated (130) before final assembly. During the measurements, the electrode is polarized cathodically by applying −0.8 V between the working electrode (gold) and the reference electrode (Ag/AgCl wire). The current between the working electrode and the reference electrode is directly proportional to the concentration of oxygen in the solution. The oxygen microelectrodes are calibrated in water equilibrated with $N_2$ and in air. The measured current is typically in the range of 10-150 pA for $N_2$ and 100-700 pA for air-saturated water. The dissolved oxygen concentrations are 0 and 7.8 mg/L in water (at 25° C. and 1 atm pressure) saturated with pure $N_2$ and in air, respectively. Two-point calibration, in $N_2$ and in air, is sufficient because the calibration curve is linear. The electrode is moved from air to $N_2$-saturated water (or vice versa) to check the response time of the electrode (time to reach 95% of the saturation value). This is typically 1-3 s. The current measured should be independent of whether the solution is stirred. A difference of 5% between the currents measured with and without stirring is considered acceptable. With calibration complete, the assembled inner sensor cylinder (818) may carefully be placed into the probe casing (803).

Figure 22:
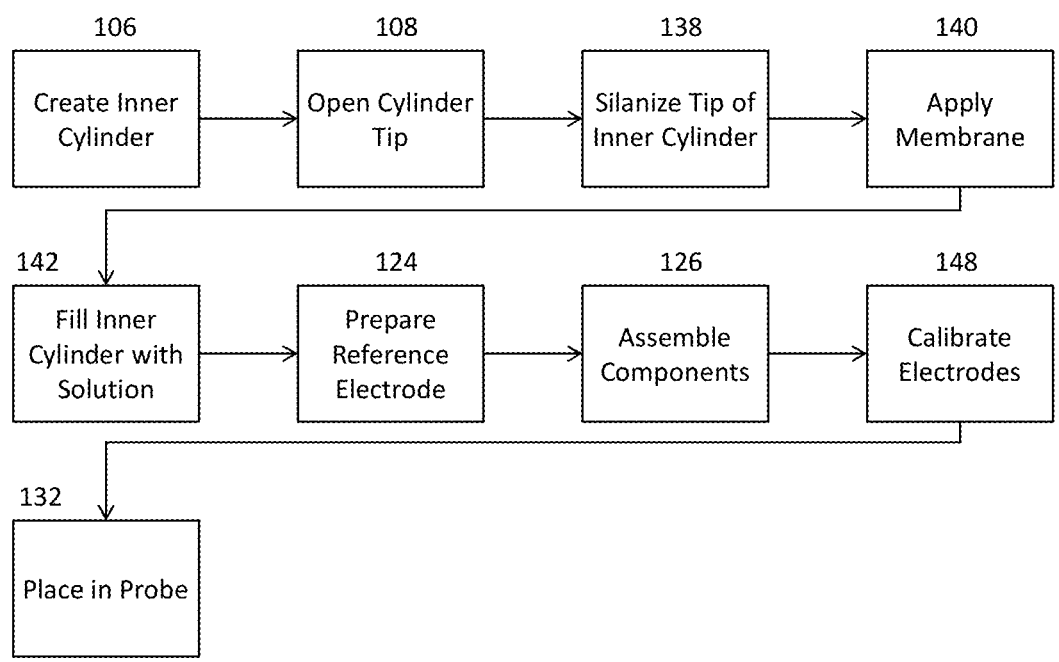
FIG. 22 is a flowchart showing an example of a set of steps that may be performed to manufacture a sensor for measuring acidity characteristics.
Figure 23:
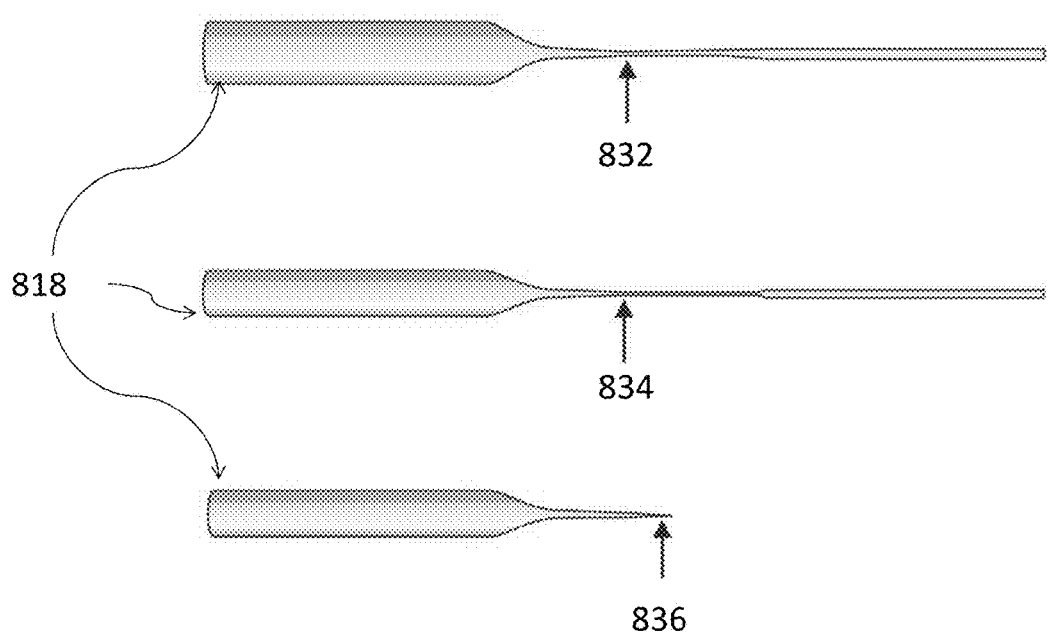
FIG. 23 shows three glass cylinders during various stages of manufacture.

FIG. 22 shows an example of a set of steps that may be performed to manufacture a sensor probe to measure pH characteristics. Initially, the inner sensor cylinder (818) should be created (106) and the tip should be opened, as described above in the context of FIG. 21. Next, the tip of the inner sensor cylinder (818) may be silanized (138). The organic liquid membrane must adhere to the glass wall of the electrode; otherwise, the aqueous electrolyte solution will find a pathway along the luminal glass surface, thus short-circuiting the membrane and destroying the membrane potential. This requirement creates some problems because LIX membranes are hydrophobic liquids and do not adhere well to hydrophilic glass surfaces. This problem is handled by making the glass surface hydrophobic through silanization. Reactive silanes replace hydroxyl groups on the glass surface and bind to it with covalent bonds, resulting in a monomolecular hydrophobic coating. Vapor treatment with N,N-dimethyltrimethylsilylamine (TMSDMA; Fluka #417-16) is a very effective and widely used silanization method. Another method is to use Fluka #85120 silanization solution. The major disadvantages of using TMSDMA are that this compound has a high vapor pressure, evaporates easily, and is extremely toxic. To silanize the tip of a pipette, the tip is briefly dipped into the silanization solution.

The micropipettes with the silane in their tips may be mounted horizontally in a petri dish and put into an oven, where they are baked at 200° C. for 15 minutes. The micropipettes are now silanized and are ready for the membrane to be applied. They may be stored in the oven at 110° C. Storing silanized pipettes for long periods should be avoided, though they may be stored in a hot oven or in desiccators to keep them dry. Despite all efforts, resilanization may be necessary if the pipettes have been stored for several days. The silanization temperatures used in different laboratories range from 110 to 200° C. but higher temperatures give better results. It has been reported that silanization may fail if the oven is contaminated with other organic substances that have evaporated and stuck to the inside surfaces of the oven. Cleaning the inside surfaces of the oven with a solvent and/or prolonged baking at a temperature much higher than that needed for silanization may help in such instances. Next, the membrane may be applied (140). Unless other types of pH microelectrodes are needed, such as glass membrane microelectrodes, ready-to-use liquid membrane solutions may be used such as "cocktails" which are commercially available for H+ from Fluka Chemie AG. The inner sensor cylinder (818) may then be filled, tip first, by dipping the silanized tip into a membrane solution and allowing capillary forces to draw the solution onto the tip.

After the tip is sealed, the inner sensor cylinder (818) may be filled with solution (142). The electrolyte filling solution should contain the ion to be measured in addition to chloride, which is required for stable operation of the Ag/AgCl electrode. To fill the inner sensor cylinder (818) with the electrolyte, a very thin pulled syringe may be used. The challenging part is to deliver the electrolyte to the thin end of the micropipette without trapping an air bubble. Problems may occur if the tip tapers at a steep angle, i.e., if its diameter changes rapidly. With this type of pipette tip, the release of pressure after filling may be followed by air being taken up into the tip. This does not happen if the tip has a gradual taper. The entire operation is done under a microscope. When the tip of the inner sensor cylinder (818) is examined under a microscope, the membrane should be about a 50-400-µm-long continuous region ending in a concave surface against the electrolyte filling solution. This also indicates proper silanization of the glass. A convex membrane-water interface, a LIX phase broken into multiple sections, and withdrawal of the LIX phase into the shank are typical signs of inadequate silanization. The reference electrode may then be placed (124) and the components may be partially assembled (126) as described in the context of FIG. 21. The electrodes may then be calibrated (148). The pH electrode may be calibrated using standard pH buffers. The microelectrode and an external reference, a SCE, may be immersed in solution of known pH and the potential difference between the internal and external reference electrodes is monitored. Once calibration is complete, the inner sensor cylinder (818) may be carefully inserted into the probe housing (803). As with other discussed sensors, the manufacture of the sensor of FIG. 22 may be accomplished by machines configured to automate one or more steps of the process. Sensors built using the steps and measurements described above in the context of FIGS. 21 and 22 have exhibited a number of advantages over sensors available in the prior art, such advantages may include a low cost of manufacture, increased accuracy and precision, increased speed of measurement, ability to recondition for further use, and other advantages.

VIII. Exemplary Sensor Body

Figure 26:
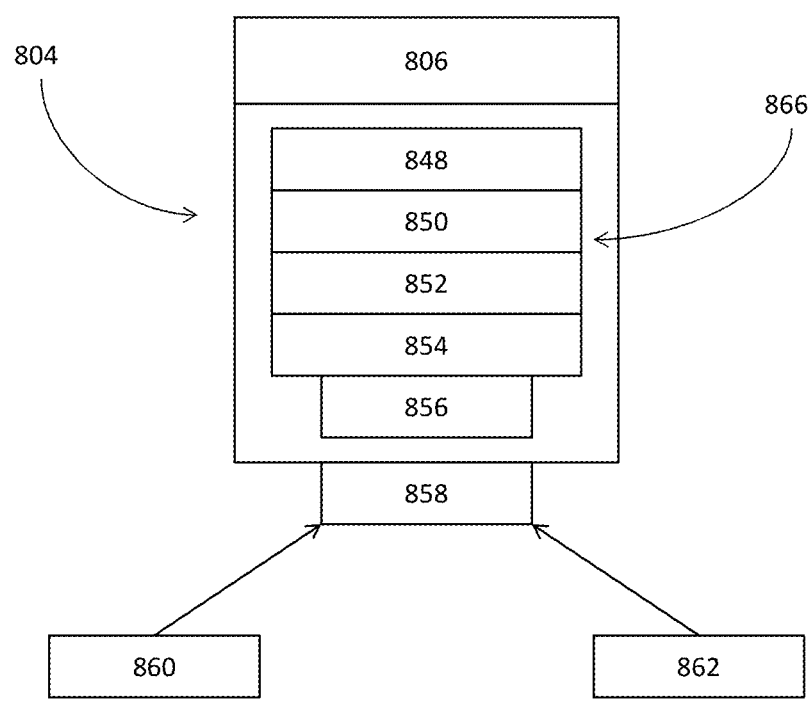
FIG. 26 shows a schematic view of an exemplary sensor body and components.

Turning now to FIG. 26, that figure shows a schematic view of an exemplary sensor body (804) and components. The sensor body casing or housing (804) may be made of plastic, metal, or another material that will allow it to be durable enough to be used with a bottle corker, and also allow it to be sealable to protect internal components. In the shown embodiment, the housing (804) is hollow and may be closed by a cap (806). The hollow portion within the housing (866) is circular and follows a form factor that allows for one or more components to be snugly stacked with the housing (804) to provide various functionality. In some embodiments, cap (806) may also have a conductive spring assembly that completes a circuit with battery (848) to allow power to be drawn from the battery (848) and conducted to other components via circuits etched on an interior wall of housing (804), or via circuits integral to the various components stacked within housing (804) that contact each other as the components are placed. The battery (848) may be one or more batteries such as a lithium CR 2016 3V battery, or other appropriate battery or power source. Components within the housing (804) may vary by embodiment, but in the shown embodiment include a base circuit (850) having a processor, a memory including one or more of a ram or secure digital storage card ("SD card"), and a Wi-Fi device, a Bluetooth device, or other wireless communication device. Also included is a first sensor circuit (852) configured to receive and process information from a first sensor probe (860) and a second sensor circuit (854) configured to receive and process information from a second sensor probe (862). The first sensor probe (860) may be, for example, a probe configured to detect oxygen within a liquid, while the second sensor (862) may be configured to detect acidity within a liquid. The first sensor circuit (852) has circuitry and devices configured to receive an electric signal from the first sensor probe (860) that is indicative of an oxygen characteristic, and is able to interpret those signals into numerical data which can be transmitted to the base circuit (850) and stored on a memory, while the second sensor circuit (854) has circuitry and devices configured to receive an electric signal from the second sensor probe (862) that is indicative of an acidity characteristic, and is able to interpret those signal into numerical data which can be stored on the memory of the base circuit (850).

A sensor input (856) is a connection that contacts with a sensor output of the first or second probe (860, 862) when the probe is screwed onto a threaded screw base receiver (858). In this manner, when the first probe (860) is attached to the screw base receiver (858), the first probe (860) connects to the sensor input (856) such that electric signals can be transmitted from the first probe (860) to the first sensor circuit (852). Since different sensor probes (860, 862) may be fitted to the screw receiver (858), a single probe body (804) may support a variety of probe sensors and, as sensors become dirty or in need of reconditioning due to their exposure to measured liquids, use of the probe body (804) may continue with a different probe sensor. Adapting the various components housed with the probe body (804) to snugly fit within the probe housing (866) allows for circuitry that would normally spread across a circuit board much larger than the area of the probe body to be fit within the probe housing (866). Accordingly, while the embodiment shown in FIG. 26 shows the circuitry spread across a base circuit (850), a first sensor circuit (852), and a second sensor circuit (854), the same functionality could be spread across as many probe body (804) form factor circuit boards as needed, though a balance between number of stacked circuits and keeping a reasonable length of the probe body (804) should be a goal.

IX. Miscellaneous

It be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

Unless explicitly stated or made implicit by dependencies upon output of a previous step, it should also be understood that many of the methods and sets of steps shown may be performed in a different order, or may be performed in parallel instead of in serial, or may be performed serially instead of in parallel. Additionally, when used in the specification and claims, it should be understood that a set is a collection of zero or more objects or things.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An apparatus comprising:
   (a) a sensor body comprising a sensor processor, a memory, and a power source;
   (b) a probe extending outwards from the sensor body, the probe comprising:

(i) a sharpened tip at the distal end;
(ii) an opening on a side exterior of the probe proximate to the sharpened tip;
(iii) a tip chamber accessible via the opening; and
(iv) a sensor intake within the tip chamber, wherein a first side of the sensor intake is accessible via the tip chamber and a second side of the sensor intake is within a capillary that is sealed from the tip chamber; and
(c) a micro-sensor within the capillary and proximate to the second side of the sensor intake, the micro-sensor situated to contact a substance entering the sensor intake from the tip chamber;
wherein the sensor processor is configured to:
(i) receive a characteristic data from the micro-sensor when the micro-sensor is in contact with the substance; and
(ii) store the set of characteristic data on the memory, wherein the set of characteristic data describes one or more characteristics of the substance.

2. The apparatus of claim 1, wherein:
(a) the sensor body is adapted to fit within a holder portion of an installation tool;
(b) when the sensor body is within the holder portion, the installation tool is usable to drive the sharpened tip through a seal of a container while maintaining the probe in a position that is perpendicular to the seal.

3. The apparatus of claim 1, wherein:
(a) the micro-sensor comprises a measuring sensor and a reference electrode;
(b) the sensor intake comprises a porous membrane adapted to allow a portion of the substance to pass from the first side to the second side and contact the micro-sensor; and
(c) the memory comprises a solid state storage.

4. The apparatus of claim 1, further comprising a communication device operable to transmit the set of characteristic data to a user device.

5. The apparatus of claim 4, wherein the sensor processor is configured to:
(a) disable the communication device and enter a low power mode;
(b) maintain the lower power mode for a user configured time;
(c) after the passage of the user configured time, exit the low power mode and enable the communication device; and
(d) transmit the set of characteristic data via the communication device only when the communication device is enabled.

6. The apparatus of claim 1, further comprising a user device comprising a user device processor, a display, and a user input device, wherein the user device is configured to receive the set of characteristic data from the memory.

7. The apparatus of claim 6, wherein the user device is further configured to:
(a) receive a set of comparable data from a remote data source;
(b) perform a comparison of the set characteristic data and the set of comparable data; and
(c) generate a user alert based upon the comparison;
wherein:
(a) the set of comparable data is associated with a first container;
(b) the set of characteristic data is associated with a second container;
(c) the comparison determines a level of similarity between the contents of the first container and the second container; and
(d) when the level of similarity does not exceed a configured threshold, the user alert indicates that the contents of the first container and the second container are dissimilar.

8. The apparatus of claim 6, wherein the user device is further configured to:
(a) associate the set of characteristic data with a first time period;
(b) receive a second set of characteristic data from the memory;
(c) associate the second set of characteristic data with a second time period;
(d) compare the set of characteristic data with the second set of characteristic data to determine a change from the first time period to the second time period; and
(e) when the change exceeds a threshold for normal change, generate a user alert indicating an unexpected change.

9. The apparatus of claim 6, wherein the set of characteristic data describes a set of measurable characteristics of the substance, and wherein the user device is further configured to:
(a) receive via the user input device a set of optimal measurements, wherein each optimal measurement of the set of optimal measurements describes a user defined preference for one characteristic of the set of measurable characteristics;
(b) after the set of measurable characteristics is received, determine if any characteristic matches an associated optimal measurement; and
(c) when a match is determined, generate a user alert indicating that one or more characteristics of the substance match the user defined preference.

10. The apparatus of claim 6, wherein the set of characteristic data is associated with a container of the substance, wherein the user device is configured to transmit a container description to a remote server, the container description comprising a description of the container, the set of characteristic data, and a time period during which set of characteristic data was created.

11. The apparatus of claim 10, wherein the user device is configured to:
(a) receive a set of container descriptions from the remote server; and
(b) display one or more of the set of container descriptions;
wherein each of the set of container descriptions comprises a historic set of characteristic data for an associated container of the substance.

12. The apparatus of claim 11, wherein:
(a) at least one of the set of container descriptions comprises an indication of improper storage for the associated container of the substance, and
(b) the indication of improper storage is determined based upon the historic set of characteristic data.

13. A method for measuring attributes of a substance comprising the steps
(a) placing a measuring device in a substance, the measuring device comprising a probe and a memory, the probe having a sharpened tip, an opening on a side exterior of the probe proximate to the sharpened tip, a tip chamber accessible via the opening, a sensor intake within the tip chamber, and a micro-sensor within a capillary proximate to the sensor intake, wherein:

(i) a liquid that enters the tip chamber via the opening is received by a first side of the sensor intake that is within the tip chamber,
(ii) the liquid contacts the micro-sensor at a second side of the sensor intake that is within the capillary, and
(iii) the capillary is sealed from the tip chamber,
(b) measuring a set of characteristic data for the substance with the micro-sensor; and
(c) storing the set of characteristic data on the memory.

14. The method of claim 13, wherein the substance is selected from the group consisting of:
(a) an alcoholic beverage;
(b) a liquid vaccine;
(c) a liquid medicine;
(d) a perfume; and
(e) a vinegar.

15. The method of claim 13, further comprising the steps:
(a) transmitting the set of characteristic data from the memory to a user device using a communication device of the measuring device; and
(b) creating a container description based on the set of characteristic data and transmitting the container description to a remote server from the user device;
wherein the container description is configured to be used by the remote server to update a set of historic container data for a container of the substance associated with the set of characteristic data.

16. The method of claim 13, wherein the set of characteristic data stored on the memory comprises a first measurement describing a characteristic of the substance from a first period of time and a second measurement describing a characteristic of the substance from a second period of time, the method further comprising:
(a) associating a container identifier with the substance, wherein the container identifier is a uniquely assigned identification data;
(a) determining an elapsed time between the first period of time and the second period of time;
(b) determining a characteristic change between the first measurement and the second measurement; and
(c) where the characteristic change during the elapsed time exceeds a configured fraud threshold, providing an indication to a remote server that the substance associated with the container identifier has been intentionally altered or changed in a suspicious manner based on the elapsed time and the characteristic change.

17. The method of claim 15, further comprising the steps:
(a) receiving, from the remote server, a set of container descriptions; and
(b) displaying, via the user device, one or more of the set of container descriptions,
wherein each of the set of container descriptions comprises a historic set of characteristic data for an associated container of the substance.

18. The method of claim 17, wherein at least one of the set of container descriptions comprises an indication of improper storage for the associated container of the substance during a time period within the historic set of characteristic data.

19. An apparatus comprising:
(a) a sensor processor;
(b) a probe comprising:
(i) a sharpened tip at a distal end of the probe;
(ii) an opening on a side exterior of the probe proximate to the sharpened tip;
(iii) a tip chamber accessible via the opening; and
(iv) a sensor intake within the tip chamber, wherein a first side of the sensor intake is accessible via the tip chamber and a second side of the sensor intake is within a capillary that is sealed from the tip chamber; and
(c) a micro-sensor within the capillary and proximate to the second side of the sensor intake in order contact a substance entering the sensor intake from the tip chamber, the micro sensor configured to provide a signal to the sensor processor based on the substance.

20. The apparatus of claim 19, wherein:
(a) the micro-sensor comprises a measuring sensor and a reference electrode;
(b) the outer diameter of the capillary is about 1 mm; and
(c) when inserted into a container through a seal, an exterior surface of the probe is adapted to prevent contact between the ambient environment and the substance within the container.

* * * * *